US010539481B2

United States Patent
(12) United States Patent
Plahey et al.

(10) Patent No.: US 10,539,481 B2
(45) Date of Patent: Jan. 21, 2020

(54) MEDICAL FLUID CASSETTE LEAK DETECTION METHODS AND DEVICES

(71) Applicant: Fresenius Medical Care Holdings, Inc., Waltham, MA (US)

(72) Inventors: Kulwinder S. Plahey, Martinez, CA (US); Jie Zhu, Antioch, CA (US); Tri Ly, Dublin, CA (US); Robert Matthew Ohline, Redwood City, CA (US); William Scott Crawford, Palo Alto, CA (US)

(73) Assignee: Fresenius Medical Care Holdings, Inc., Waltham, WA (US)

( * ) Notice: Subject to any disclaimer, the term of this patent is extended or adjusted under 35 U.S.C. 154(b) by 274 days.

(21) Appl. No.: 15/399,043

(22) Filed: Jan. 5, 2017

(65) Prior Publication Data

US 2017/0115178 A1 Apr. 27, 2017

Related U.S. Application Data

(62) Division of application No. 13/804,198, filed on Mar. 14, 2013, now Pat. No. 9,561,323.

(51) Int. Cl.

*G01M 3/32* (2006.01)
*A61M 5/142* (2006.01)

(Continued)

(52) U.S. Cl.

CPC ............ *G01M 3/3218* (2013.01); *A61M 1/16* (2013.01); *A61M 1/28* (2013.01); *A61M 1/282* (2014.02);

(Continued)

(58) Field of Classification Search

CPC .......... A61M 1/16; A61M 1/28; A61M 1/282; A61M 1/288; A61M 2205/07;

(Continued)

(56) References Cited

U.S. PATENT DOCUMENTS

| | | | |
|---|---|---|---|
| 329,773 | A | 11/1885 | Perry |
| 2,383,193 | A | 8/1945 | Herbert |

(Continued)

FOREIGN PATENT DOCUMENTS

| | | |
|---|---|---|
| CN | 101193669 | 6/2008 |
| DE | 2628238 | 1/1978 |

(Continued)

OTHER PUBLICATIONS

Avolio, Glenn, "Principles of Rotary Optical Encoders," Sensors Journal of Machine Perception, vol. 10, No. 4, pp. 10-18, 1993.

(Continued)

*Primary Examiner* — John Fitzgerald
(74) *Attorney, Agent, or Firm* — Fish & Richardson P.C.

(57) ABSTRACT

A method is provided for detecting leaks in a disposable medical fluid cassette that includes a base and a flexible membrane attached to the base in such a way that the base and the flexible membrane cooperate to at least partially form a fluid passageway. The method includes applying a first force to the flexible membrane, measuring a first physical property of a system that includes the medical fluid cassette a medical fluid pumping machine, removing the first force from the flexible membrane, applying a second force to the flexible membrane, measuring a second physical property of the system, and determining whether the medical fluid cassette leaks based on a comparison of the first physical property and the second physical property.

10 Claims, 11 Drawing Sheets

140
112
165B
153B
163B
138B
163A
153A
167
165A
138A
156
167
167

(51) Int. Cl.
*A61M 1/16* (2006.01)
*A61M 1/28* (2006.01)
*G01M 3/36* (2006.01)

(52) U.S. Cl.
CPC ............ *A61M 1/288* (2014.02); *A61M 5/142* (2013.01); *G01M 3/3272* (2013.01); *G01M 3/36* (2013.01); *A61M 2205/07* (2013.01); *A61M 2205/12* (2013.01); *A61M 2205/121* (2013.01); *A61M 2205/123* (2013.01); *A61M 2205/15* (2013.01); *A61M 2205/3331* (2013.01); *A61M 2205/50* (2013.01)

(58) Field of Classification Search
CPC ........ A61M 2205/12; A61M 2205/121; A61M 2205/123; A61M 2205/15; A61M 2205/3331; A61M 2205/50; A61M 5/142; G01M 3/3218; G01M 3/3272; G01M 3/36
See application file for complete search history.

(56) References Cited

U.S. PATENT DOCUMENTS 2,529,028 A 11/1950 Landon
2,658,526 A 11/1953 Porter
2,711,134 A 6/1955 Hughes
2,755,745 A 7/1956 Lewis
2,871,795 A 2/1959 Smith
2,886,281 A 5/1959 Canalizo
3,083,943 A 4/1963 Stewart et al.
3,323,786 A 6/1967 Boschi
3,556,465 A 1/1971 Little
3,689,025 A 9/1972 Kiser
3,741,687 A 6/1973 Nystroem
3,751,972 A 8/1973 Hass
3,927,955 A 12/1975 Spinosa et al.
3,966,358 A 6/1976 Heimes et al.
3,973,249 A 8/1976 Yokote et al.
3,985,135 A 10/1976 Carpenter et al.
4,026,669 A 5/1977 Leonard et al.
4,047,844 A 9/1977 Robinson
4,091,812 A 5/1978 Helixon et al.
4,121,584 A 10/1978 Turner et al.
4,152,098 A 5/1979 Moody et al.
4,158,530 A 6/1979 Bernstein
4,178,940 A 12/1979 Au
4,188,819 A 2/1980 Egee et al.
4,273,121 A 6/1981 Jassawalla
4,303,376 A 12/1981 Siekmann
4,304,260 A 12/1981 Turner et al.
4,322,201 A 3/1982 Archibald
4,333,452 A 6/1982 Au
4,370,983 A 2/1983 Lichtenstein
4,382,753 A 5/1983 Archibald
4,410,322 A 10/1983 Archibald
4,412,553 A 11/1983 Kopp et al.
4,436,620 A 3/1984 Bellotti et al.
4,453,932 A 6/1984 Pastrone
4,479,760 A 10/1984 Bilstad et al.
4,479,761 A 10/1984 Bilstad et al.
4,479,762 A 10/1984 Bilstad et al.
4,490,621 A 12/1984 Watabe et al.
4,536,201 A 8/1985 Brorsson et al.
4,558,715 A 12/1985 Walton et al.
4,569,378 A 2/1986 Bergandy
4,583,920 A 4/1986 Lindner
4,597,412 A 7/1986 Stark
4,623,328 A 11/1986 Hartranft
4,628,499 A 12/1986 Hammett
4,639,245 A 1/1987 Pastrone et al.
4,643,713 A 2/1987 Viitala
4,657,490 A 4/1987 Abbott
4,662,598 A 5/1987 Weingarten
4,662,906 A 5/1987 Matkovich et al.
4,676,467 A 6/1987 Palsulich
4,690,621 A 9/1987 Swain
4,697,452 A 10/1987 Prakken
4,703,913 A 11/1987 Hunkapiller
4,705,259 A 11/1987 Dolhen et al.
4,710,166 A 12/1987 Thompson et al.
4,715,215 A 12/1987 Perhach et al.
4,735,558 A 4/1988 Kienholz et al.
4,778,451 A 10/1988 Kamen
4,808,161 A 2/1989 Kamen
4,818,186 A 4/1989 Pastrone et al.
4,826,482 A 5/1989 Kamen
4,840,542 A 6/1989 Abbott
4,842,584 A 6/1989 Pastrone
4,846,636 A 7/1989 Danby et al.
4,850,980 A 7/1989 Lentz et al.
4,858,883 A 8/1989 Webster
4,902,282 A 2/1990 Bellotti et al.
4,906,260 A 3/1990 Emheiser et al.
4,922,746 A 5/1990 Hulsman et al.
4,927,411 A 5/1990 Pastrone et al.
4,950,134 A 8/1990 Bailey et al.
4,974,754 A 12/1990 Wirz
4,976,162 A 12/1990 Kamen
4,995,864 A 2/1991 Bartholomew et al.
4,997,464 A 3/1991 Kopf
5,000,664 A 3/1991 Lawless et al.
5,002,471 A 3/1991 Perlov
5,006,050 A 4/1991 Cooke et al.
5,036,886 A 8/1991 Olsen et al.
5,061,236 A 10/1991 Sutherland et al.
5,088,515 A 2/1992 Kamen
5,098,262 A 3/1992 Wecker et al.
5,100,380 A 3/1992 Epstein et al.
5,100,699 A 3/1992 Roeser
5,116,021 A 5/1992 Faust et al.
5,116,316 A 5/1992 Sertic et al.
5,146,713 A 9/1992 Grafius
5,151,019 A 9/1992 Danby et al.
5,167,837 A 12/1992 Snodgrass et al.
5,171,029 A 12/1992 Maxwell et al.
5,178,182 A 1/1993 Kamen
5,193,990 A 3/1993 Kamen et al.
5,211,201 A 5/1993 Kamen et al.
5,241,985 A 9/1993 Faust et al.
5,247,434 A 9/1993 Peterson et al.
5,249,932 A 10/1993 Van Bork
5,252,044 A 10/1993 Raines et al.
5,259,352 A 11/1993 Gerhardy et al.
5,267,956 A 12/1993 Beuchat
5,279,556 A 1/1994 Goi et al.
5,302,093 A 4/1994 Owens et al.
5,324,422 A 6/1994 Colleran et al.
5,330,425 A 7/1994 Utterberg
5,336,053 A 8/1994 Wynkoop
5,342,182 A 8/1994 Montoya et al.
5,344,292 A 9/1994 Rabenau et al.
5,350,357 A 9/1994 Kamen et al.
D351,470 S 10/1994 Scherer et al.
5,353,837 A 10/1994 Faust
5,378,126 A 1/1995 Abrahamson et al.
5,395,351 A 3/1995 Munsch
5,413,626 A 5/1995 Bartsch
5,415,528 A 5/1995 Ogden et al.
5,421,208 A 6/1995 Packard et al.
5,421,823 A 6/1995 Kamen et al.
5,427,509 A 6/1995 Chapman et al.
5,431,626 A 7/1995 Bryant et al.
5,431,627 A 7/1995 Pastrone et al.
5,431,634 A 7/1995 Brown
5,438,510 A 8/1995 Bryant et al.
5,441,636 A 8/1995 Chevallet et al.
5,445,506 A 8/1995 Afflerbaugh et al.
5,447,286 A 9/1995 Kamen et al.
5,462,416 A 10/1995 Dennehey et al.
5,462,417 A 10/1995 Chapman
5,474,683 A 12/1995 Bryant et al.
5,478,211 A 12/1995 Dominiak et al.
5,480,294 A 1/1996 DiPerna et al.

(56) References Cited

U.S. PATENT DOCUMENTS 5,482,438 A 1/1996 Anderson et al.
5,482,440 A 1/1996 Dennehey et al.
5,482,446 A 1/1996 Williamson et al.
5,484,239 A 1/1996 Chapman et al.
5,486,286 A 1/1996 Peterson et al.
5,514,069 A 5/1996 Brown et al.
5,538,405 A 7/1996 Patno et al.
5,540,568 A 7/1996 Rosen et al.
5,547,453 A 8/1996 DiPerna
5,551,850 A 9/1996 Williamson et al.
5,551,941 A 9/1996 Howell
5,551,942 A 9/1996 Brown et al.
5,554,013 A 9/1996 Owens et al.
5,570,716 A 11/1996 Kamen et al.
5,573,385 A 11/1996 Chevallier
5,578,070 A 11/1996 Utterberg
5,586,868 A 12/1996 Lawless et al.
5,588,816 A 12/1996 Abbott et al.
5,593,290 A 1/1997 Greisch et al.
5,609,572 A 3/1997 Lang
5,614,677 A 3/1997 Wamsiedler et al.
5,628,908 A 5/1997 Kamen et al.
5,630,710 A 5/1997 Tune et al.
5,634,896 A 6/1997 Bryant et al.
5,640,995 A 6/1997 Packard et al.
5,641,405 A 6/1997 Keshaviah et al.
5,641,892 A 6/1997 Larkins et al.
5,643,205 A 7/1997 Utterberg
5,645,531 A 7/1997 Thompson et al.
5,658,133 A 8/1997 Anderson et al.
5,669,764 A 9/1997 Behringer et al.
5,674,404 A 10/1997 Kenley et al.
5,690,602 A 11/1997 Brown et al.
D390,654 S 2/1998 Alsberg et al.
5,713,865 A 2/1998 Manning et al.
5,713,888 A 2/1998 Neuenfeldt et al.
5,718,567 A 2/1998 Rapp et al.
5,741,125 A 4/1998 Neftel et al.
5,746,708 A 5/1998 Giesler et al.
5,755,683 A 5/1998 Houle et al.
5,764,034 A 6/1998 Bowman et al.
5,769,387 A 6/1998 Perez
5,771,914 A 6/1998 Ling et al.
5,772,635 A 6/1998 Dastur et al.
5,772,637 A 6/1998 Heinzmann et al.
5,775,371 A 7/1998 Pan et al.
5,782,575 A 7/1998 Vincent et al.
5,782,805 A 7/1998 Meinzer et al.
5,799,207 A 8/1998 Wang et al.
5,816,779 A 10/1998 Lawless et al.
5,840,151 A 11/1998 Munsch
5,842,841 A 12/1998 Danby et al.
5,843,035 A 12/1998 Bowman et al.
5,868,696 A 2/1999 Giesler et al.
5,873,853 A 2/1999 Keilman et al.
5,902,096 A 5/1999 Behringer et al.
5,906,598 A 5/1999 Giesler et al.
5,921,951 A 7/1999 Morris
5,925,011 A 7/1999 Faict et al.
5,934,885 A 8/1999 Farrell et al.
5,935,099 A 8/1999 Peterson et al.
5,938,634 A 8/1999 Packard
5,984,897 A 11/1999 Petersen et al.
5,989,423 A 11/1999 Kamen et al.
5,993,174 A 11/1999 Konishi
5,996,634 A 12/1999 Dennehey et al.
6,013,057 A 1/2000 Danby et al.
6,036,668 A 3/2000 Mathis
6,036,680 A 3/2000 Horne et al.
6,041,801 A 3/2000 Gray et al.
6,053,191 A 4/2000 Hussey
6,065,389 A 5/2000 Riedlinger
6,065,941 A 5/2000 Gray et al.
6,068,612 A 5/2000 Bowman et al.
6,074,359 A 6/2000 Keshaviah et al.
6,079,959 A 6/2000 Kingsford et al.
6,099,492 A 8/2000 Le Boeuf
6,106,246 A 8/2000 Steck et al.
6,110,410 A 8/2000 Owens et al.
6,118,207 A 9/2000 Ormerod et al.
6,129,517 A 10/2000 Danby et al.
6,132,187 A 10/2000 Ericson
6,136,565 A 10/2000 Best et al.
6,152,705 A 11/2000 Kennedy et al.
6,154,605 A 11/2000 Aonuma
6,164,621 A 12/2000 Bouchard et al.
6,165,154 A 12/2000 Gray et al.
6,168,394 B1 1/2001 Forman et al.
6,178,996 B1 1/2001 Suzuki
6,179,801 B1 1/2001 Holmes et al.
6,184,356 B1 2/2001 Anderson et al.
6,189,857 B1 2/2001 Zeger et al.
6,196,987 B1 3/2001 Holmes et al.
6,200,287 B1 3/2001 Keller et al.
6,206,644 B1 3/2001 Pereira et al.
6,208,107 B1 3/2001 Maske et al.
6,210,361 B1 4/2001 Kamen et al.
6,220,295 B1 4/2001 Bouchard et al.
6,223,130 B1 4/2001 Gray et al.
6,227,807 B1 5/2001 Chase
6,227,824 B1 5/2001 Stehr
6,228,047 B1 5/2001 Dadson
6,228,271 B1 5/2001 Cote
6,229,753 B1 5/2001 Kono et al.
6,231,537 B1 5/2001 Holmes et al.
6,234,989 B1 5/2001 Brierton et al.
6,250,502 B1 6/2001 Cote et al.
6,261,065 B1 7/2001 Nayak et al.
6,267,242 B1 7/2001 Nagata et al.
6,270,673 B1 8/2001 Belt et al.
6,272,903 B1 8/2001 Shafer
6,280,406 B1 8/2001 Dolecek et al.
6,281,145 B1 8/2001 Deguchi et al.
6,284,142 B1 9/2001 Muller
6,285,155 B1 9/2001 Maske et al.
6,286,566 B1 9/2001 Cline et al.
6,294,094 B1 9/2001 Muller et al.
6,296,450 B1 10/2001 Westberg et al.
6,297,322 B1 10/2001 Ding et al.
6,302,653 B1 10/2001 Bryant et al.
6,315,707 B1 11/2001 Smith et al.
6,315,754 B1 11/2001 Daoud et al.
6,316,864 B1 11/2001 Ormerod
6,322,488 B1 11/2001 Westberg et al.
6,325,775 B1 12/2001 Thom et al.
6,337,049 B1 1/2002 Tamari
RE37,553 E 2/2002 Ciavarini et al.
6,343,614 B1 2/2002 Gray et al.
6,348,156 B1 2/2002 Vishnoi et al.
6,361,518 B1 3/2002 Brierton et al.
6,364,857 B1 4/2002 Gray et al.
6,367,669 B1 4/2002 Au et al.
6,382,923 B1 5/2002 Gray
6,383,158 B1 5/2002 Utterberg et al.
6,402,486 B1 6/2002 Steck et al.
6,406,276 B1 6/2002 Normand et al.
6,409,696 B1 6/2002 Toavs et al.
6,416,293 B1 7/2002 Bouchard et al.
6,419,822 B2 7/2002 Muller et al.
6,455,676 B1 9/2002 Weickert et al.
6,471,855 B1 10/2002 Odak et al.
6,481,980 B1 11/2002 Vandlik et al.
6,484,383 B1 11/2002 Herklotz
6,489,896 B1 12/2002 Platt et al.
6,491,656 B1 12/2002 Morris
6,494,694 B2 12/2002 Lawless et al.
6,497,674 B1 12/2002 Steele et al.
6,497,676 B1 12/2002 Childers et al.
6,503,062 B1 1/2003 Gray et al.
6,514,225 B1 2/2003 Utterberg et al.
6,519,569 B1 2/2003 White et al.
6,520,747 B2 2/2003 Gray et al.
6,524,231 B1 2/2003 Westberg et al.
6,529,573 B2 3/2003 Olsher et al.

(56) References Cited

U.S. PATENT DOCUMENTS 6,537,445 B2 3/2003 Muller
6,542,761 B1 4/2003 Jahn et al.
6,558,343 B1 5/2003 Neftel
6,572,604 B1 6/2003 Platt et al.
6,579,253 B1 6/2003 Burbank et al.
6,592,542 B2 7/2003 Childers et al.
6,595,948 B2 7/2003 Suzuki et al.
6,603,229 B1 8/2003 Toye
6,604,908 B1 8/2003 Bryant et al.
6,645,166 B2 11/2003 Scheunert et al.
6,645,177 B1 11/2003 Shearn
6,648,861 B2 11/2003 Platt et al.
6,663,359 B2 12/2003 Gray
6,670,323 B1 12/2003 Looker et al.
6,672,841 B1 1/2004 Herklotz et al.
6,695,593 B1 2/2004 Steck et al.
6,695,803 B1 2/2004 Robinson et al.
6,709,417 B1 3/2004 Houle et al.
6,716,004 B2 4/2004 Vandlik et al.
6,723,062 B1 4/2004 Westberg et al.
6,725,726 B1 4/2004 Adolfs et al.
6,726,656 B2 4/2004 Kamen et al.
6,730,055 B2 5/2004 Bainbridge et al.
6,743,201 B1 6/2004 Dönig et al.
6,746,514 B2 6/2004 Bedingfield et al.
6,749,403 B2 6/2004 Bryant et al.
6,752,172 B2 6/2004 Lauer
6,752,599 B2 6/2004 Park
6,755,801 B2 6/2004 Utterberg et al.
6,758,975 B2 7/2004 Peabody et al.
6,759,007 B1 7/2004 Westberg et al.
6,759,014 B2 7/2004 Dales et al.
6,764,460 B2 7/2004 Dolecek et al.
6,764,761 B2 7/2004 Eu et al.
6,768,425 B2 7/2004 Flaherty et al.
6,774,517 B2 8/2004 Kowalski et al.
6,790,014 B2 9/2004 Bowen
6,790,195 B2 9/2004 Steele et al.
6,790,198 B1 9/2004 White et al.
6,800,054 B2 10/2004 Westberg et al.
6,808,369 B2 10/2004 Gray et al.
6,814,547 B2 11/2004 Childers et al.
6,821,432 B2 11/2004 Metzner
6,828,125 B1 12/2004 Hoffman et al.
6,846,161 B2 1/2005 Kline et al.
6,852,090 B2 2/2005 Burbank et al.
6,869,538 B2 3/2005 Yu et al.
6,905,479 B1 6/2005 Bouchard et al.
6,929,751 B2 8/2005 Bowman et al.
6,939,111 B2 9/2005 Huitt et al.
6,949,079 B1 9/2005 Westberg et al.
6,953,323 B2 10/2005 Childers et al.
6,957,952 B1 10/2005 Steck et al.
6,984,218 B2 1/2006 Nayak et al.
7,021,148 B2 4/2006 Kuhn et al.
7,029,245 B2 4/2006 Maianti et al.
7,033,539 B2 4/2006 Krensky et al.
7,041,076 B1 5/2006 Westberg et al.
7,044,432 B2 5/2006 Beden et al.
7,049,406 B2 5/2006 Weickert et al.
7,083,719 B2 8/2006 Bowman et al.
7,087,036 B2 8/2006 Busby et al.
7,107,837 B2 9/2006 Lauman et al.
7,115,107 B2 10/2006 Delnevo et al.
7,115,228 B2 10/2006 Lundtveit et al.
7,147,613 B2 12/2006 Burbank et al.
7,153,286 B2 12/2006 Busby et al.
7,160,087 B2 1/2007 Fathallah et al.
7,166,231 B2 1/2007 Westberg et al.
7,175,606 B2 2/2007 Bowman et al.
7,195,607 B2 3/2007 Westberg et al.
7,211,560 B2 5/2007 Looker et al.
7,232,435 B2 6/2007 Hildebrand et al.
7,236,936 B2 6/2007 White et al.
7,238,164 B2 7/2007 Childers et al.
7,255,680 B1 8/2007 Gharib
7,258,534 B2 8/2007 Fathallah et al.
7,261,559 B2 8/2007 Smith et al.
7,267,661 B2 9/2007 Susi
7,273,465 B2 9/2007 Pish
7,306,578 B2 12/2007 Gray et al.
7,331,935 B2 2/2008 Barere
7,338,469 B2 3/2008 Barker et al.
7,338,472 B2 3/2008 Sheam
7,345,025 B2 3/2008 Symonds et al.
7,347,836 B2 3/2008 Peterson et al.
7,390,311 B2 6/2008 Hildebrand et al.
7,398,183 B2 7/2008 Holland et al.
7,399,637 B2 7/2008 Wright et al.
7,404,809 B2 7/2008 Susi
7,410,475 B2 8/2008 Krensky et al.
7,422,905 B2 9/2008 Clague et al.
7,454,314 B2 11/2008 Holland et al.
7,461,968 B2 12/2008 Demers et al.
7,490,021 B2 2/2009 Holland et al.
7,500,962 B2 3/2009 Childers et al.
7,517,387 B2 4/2009 Chevallet et al.
7,553,295 B2 6/2009 Susi
7,556,616 B2 7/2009 Fathallah et al.
7,575,564 B2 8/2009 Childers
7,618,948 B2 11/2009 Kaemmerer
7,645,258 B2 1/2010 White et al.
7,648,627 B2 1/2010 Beden et al.
7,654,976 B2 2/2010 Peterson et al.
7,662,133 B2 2/2010 Scarborough et al.
7,662,286 B2 2/2010 Childers et al.
7,699,966 B2 4/2010 Qin et al.
7,717,682 B2 5/2010 Orr
7,789,849 B2 9/2010 Busby et al.
7,815,595 B2 10/2010 Busby et al.
8,038,640 B2 10/2011 Orr
8,197,231 B2 6/2012 Orr
8,197,439 B2 6/2012 Wang et al.
8,206,338 B2 6/2012 Childers et al.
8,292,594 B2 10/2012 Tracey et al.
8,366,921 B2 2/2013 Beden et al.
8,409,441 B2 4/2013 Wilt
8,562,834 B2 10/2013 Kamen et al.
8,721,879 B2 5/2014 van der Merwe et al.
8,900,174 B2 12/2014 Childers
9,561,323 B2 * 2/2017 Plahey .................. A61M 1/282
2001/0034502 A1 10/2001 Moberg et al.
2001/0037763 A1 11/2001 Deguchi et al.
2002/0045851 A1 4/2002 Suzuki et al.
2002/0062109 A1 5/2002 Lauer
2002/0072718 A1 6/2002 Brugger et al.
2002/0107474 A1 8/2002 Noack
2002/0147423 A1 10/2002 Burbank et al.
2003/0018395 A1 1/2003 Crnkovich et al.
2003/0028144 A1 2/2003 Duchon et al.
2003/0029451 A1 2/2003 Blair et al.
2003/0042181 A1 3/2003 Metzner
2003/0100882 A1 5/2003 Beden et al.
2003/0136189 A1 7/2003 Lauman et al.
2003/0194332 A1 10/2003 Jahn et al.
2003/0200812 A1 10/2003 Kuhn et al.
2003/0204162 A1 10/2003 Childers et al.
2003/0217957 A1 11/2003 Bowman et al.
2003/0217961 A1 11/2003 Hopping
2003/0217975 A1 11/2003 Yu et al.
2003/0218623 A1 11/2003 Krensky et al.
2003/0220599 A1 11/2003 Lundtveit et al.
2003/0220605 A1 11/2003 Bowman et al.
2003/0220607 A1 11/2003 Busby et al.
2003/0220608 A1 11/2003 Huitt et al.
2003/0220609 A1 11/2003 Childers et al.
2003/0220627 A1 11/2003 Distler et al.
2004/0001766 A1 1/2004 Maianti et al.
2004/0010223 A1 1/2004 Busby et al.
2004/0019313 A1 1/2004 Childers et al.
2004/0019320 A1 1/2004 Childers et al.
2004/0031756 A1 2/2004 Suzuki et al.
2004/0064080 A1 4/2004 Cruz et al.
2004/0067161 A1 4/2004 Axelsson

(56) References Cited

U.S. PATENT DOCUMENTS

2004/0082903 A1 4/2004 Micheli
2004/0084647 A1 5/2004 Beden et al.
2004/0109769 A1 6/2004 Jahn et al.
2004/0115068 A1 6/2004 Hansen et al.
2004/0135078 A1 7/2004 Mandro et al.
2004/0136843 A1 7/2004 Jahn et al.
2004/0156745 A1 8/2004 Vandlik et al.
2004/0195190 A1 10/2004 Min et al.
2004/0238416 A1 12/2004 Burbank et al.
2005/0054968 A1 3/2005 Giannella
2005/0056081 A1* 3/2005 Gocho ................ G01M 3/2815 73/40
2005/0126998 A1 6/2005 Childers
2005/0230292 A1 10/2005 Beden et al.
2006/0002823 A1 1/2006 Feldstein
2006/0079766 A1 4/2006 Neet et al.
2006/0079826 A1 4/2006 Beden et al.
2006/0195064 A1 8/2006 Plahey et al.
2007/0112297 A1 5/2007 Plahey et al.
2007/0149913 A1 6/2007 Busby et al.
2007/0193940 A1 8/2007 Duchamp et al.
2007/0213651 A1 9/2007 Busby et al.
2007/0213653 A1 9/2007 Childers et al.
2007/0269340 A1 11/2007 Dannenmaier et al.
2007/0278155 A1 12/2007 Lo et al.
2008/0033346 A1 2/2008 Childers et al.
2008/0077068 A1 3/2008 Orr
2008/0125693 A1 5/2008 Gavin et al.
2008/0208103 A1 8/2008 Demers et al.
2008/0216898 A1 9/2008 Grant et al.
2008/0253912 A1 10/2008 Demers et al.
2009/0004033 A1 1/2009 Demers et al.
2009/0007642 A1 1/2009 Busby et al.
2009/0099498 A1 4/2009 Demers et al.
2009/0137940 A1 5/2009 Orr
2009/0169402 A1 7/2009 Stenberg
2009/0212248 A1 8/2009 Kozak
2010/0211044 A1 8/2010 Dacquay et al.
2010/0241062 A1 9/2010 Morris et al.
2010/0286614 A1 11/2010 Ring
2011/0015610 A1 1/2011 Plahey et al.
2011/0020156 A1 1/2011 Van Brunt et al.
2011/0092895 A1 4/2011 Yardimci et al.
2011/0125085 A1 5/2011 McGill et al.
2011/0137237 A1 6/2011 Prisco et al.
2011/0293450 A1 12/2011 Grimes et al.
2012/0065581 A1 3/2012 Childers et al.
2012/0083729 A1 4/2012 Childers
2012/0123322 A1 5/2012 Scarpaci et al.
2012/0209169 A1 8/2012 Morris et al.
2012/0224984 A1 9/2012 Orr
2012/0230844 A1 9/2012 Farrell et al.
2012/0232469 A1 9/2012 Medina
2012/0271226 A1 10/2012 Farrell et al.
2012/0308412 A1 12/2012 Rochat
2013/0118961 A1 5/2013 Beden et al.
2013/0118970 A1 5/2013 Beden et al.
2013/0184638 A1 7/2013 Scarpaci et al.
2013/0330208 A1 12/2013 Ly et al.
2013/0331774 A1 12/2013 Farrell et al.
2014/0260551 A1 9/2014 Gray et al.
2014/0260556 A1 9/2014 Gray et al.
2014/0276421 A1* 9/2014 Plahey .................. A61M 1/282 604/151
2014/0319035 A1 10/2014 Burbank et al.
2015/0082867 A1 3/2015 Childers
2017/0115178 A1* 4/2017 Plahey .................. A61M 1/282

FOREIGN PATENT DOCUMENTS

DE 2827648 1/1979
DE 4006785 9/1990
DE 4336336 5/1994
DE 19653325 6/1998
DE 19837667 3/2000
DE 19919572 A1 11/2000
DE 10042324 2/2002
DE 10046651 4/2002
DE 19919572 C2 4/2002
DE 10053441 5/2002
DE 69618766 8/2002
DE 10143137 4/2003
DE 10157924 6/2003
DE 102007059239 6/2009
EP 257279 A1 3/1988
EP 0406562 A2 1/1991
EP 0314379 8/1991
EP 0410125 B1 8/1993
EP 0728509 8/1996
EP 0848193 6/1998
EP 0856321 8/1998
EP 0947814 B2 10/1999
EP 0956876 A1 11/1999
EP 1529545 5/2005
EP 1680155 B1 2/2012
GB 2101232 A 1/1983
GB 1483702 8/1997
GB 2331796 6/1999
JP 2289259 11/1990
JP 0396850 A 4/1991
JP 04191755 7/1992
JP 06154314 6/1994
JP 06002650 11/1994
JP 08028722 3/1996
JP 11347115 12/1999
JP 2000070358 3/2000
JP 2000346214 12/2000
JP 200295741 4/2002
JP 2005218709 A 8/2005
WO 8402473 7/1984
WO 8601115 2/1986
WO WO8601115 A1 2/1986
WO WO1994015660 A1 7/1994
WO 9420155 9/1994
WO 9625064 A2 8/1996
WO 1997016214 5/1997
WO 1997037703 10/1997
WO 9822165 5/1998
WO WO1998022167 A1 5/1998
WO 0023140 4/2000
WO 0033898 6/2000
WO 0117605 3/2001
WO 0225146 3/2002
WO 0225225 3/2002
WO WO 2006/120415 11/2006
WO WO2007006030 A3 6/2007
WO 2009071069 6/2009
WO WO2009094179 A2 7/2009
WO WO2011045167 A1 4/2011

OTHER PUBLICATIONS

Gambro®, "DEHP-free cartridge blood sets," © Nov. 2004, Gambro, Inc., Lakewood, CO, 4 pp.
Gambro®, Prisma® HF 1000, "For Increased Filtration Capacity", © Aug. 2001, Gambro Renal Products, Inc., Lakewood, CO, 2 pp.
Gambro®, "Prisma® M60 and M100 Pre-Pump Infusion Sets—Introducing: The unique solution that enables Physicians to choose a predilution method that meets the needs of their patients", © 2004, Gambro Inc., Lakewood, CO, 4 pp.
Gambro®, "Prismaflex™ anticipating critical care needs and taking our innovative response . . . to new heights," © 2004, Gambro Inc., Lakewood, CO, 8 pp.
Liberty Cycler Operator's Manual, 2003-2004.
Manns et al., "The acu-men: A new device for continuous renal replacement therapy in acute renal failure," Kidney International, vol. 54, pp. 268-274, 1998.
Newton IQ Cycler Operator Manual, Part No. 470203 Rev. F, 2000-2006.
Operator's Instructions, Fresenius 90/2 Peritoneal Therapy Cycler, Part No. 470016, Rev. B, 1991.

(56) References Cited

OTHER PUBLICATIONS

Operator's Manual, Serena, Program Version 3.xx—English, 2002.
Sleep Safe Operating Instructions, Software Version 0.9, Part No. 677 805 1; Aug. 2000.
Sleep Safe Technical Manual, Part No. 677 807 1; Aug. 2000.
Bolegoh, Gordon, "Pumps: Reference Guide", p. 24, 3rd edition, 2001.
Ronco et al, "Evolution of Machines for Automated Peritoneal Dialysis", in Automated Peritoneal Dialysis, Contributions to Nephrology, vol. 129, pp. 142-161, 1999.
Sleep Safe Operating Instructions, Software Version 0.5, Apr. 1999.
Sleep Safe Operating Instructions, Software Version 1.0, Oct. 2000.
Sleep Safe Technical Manual, Dec. 2001.
Sleep Safe Operating Instructions, Jan. 2002.
Sleep Safe Communicating Therapy, Mar. 1998.
Sleep Safe Kommunizierte Therapie, May 1998.
Innovative Technologies in Peritoneal Dialysis, Sleep Safe Concept, Oct. 13, 1999 (4 attachments).
TL™ Pump Brochure, TL Systems Corporation, Apr. 1975.
Notification of Transmittal of the International Search Report and the Written Opinion of the International Search Authority for corresponding PCT Application No. PCT/US2014/019523, dated Jun. 5, 2014, 9 pages.

* cited by examiner

MEDICAL FLUID CASSETTE LEAK DETECTION METHODS AND DEVICES

CROSS-REFERENCE TO RELATED APPLICATION

This application is a divisional of and claims priority under 35 U.S.C. § 120 to U.S. Ser. No. 13/804,198, filed Mar. 14, 2013, now U.S. Pat. No. 9,561,323, which is hereby incorporated by reference in its entirety.

TECHNICAL FIELD

This disclosure relates to medical fluid cassette leak detection methods and devices.

BACKGROUND

Dialysis is a treatment used to support a patient with insufficient renal function. The two principal dialysis methods are hemodialysis and peritoneal dialysis.

During hemodialysis ("HD"), the patient's blood is passed through a dialyzer of a dialysis machine while also passing dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), a patient's peritoneal cavity is periodically infused with dialysate. The membranous lining of the patient's peritoneum acts as a natural semi-permeable membrane that allows diffusion and osmosis exchanges to take place between the solution and the blood stream. These exchanges across the patient's peritoneum, like the continuous exchange across the dialyzer in HD, result in the removal of waste products, including solutes like urea and creatinine, from the blood, and regulate the levels of other substances, such as sodium and water, in the blood.

Many PD machines are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle.

SUMMARY

In some aspects, a method of detecting leaks in a disposable medical fluid cassette is provided. The medical fluid cassette includes a base and a flexible membrane attached to the base in such a way that the base and the flexible membrane cooperate to at least partially form a fluid passageway. The method includes applying a first force to the flexible membrane; measuring a first physical property of a system that includes the medical fluid cassette and a medical fluid pumping machine while the first force is applied to the flexible membrane; removing the first force from the flexible membrane; applying a second force to the flexible membrane; measuring a second physical property of the system that includes the medical fluid cassette and the medical fluid pumping machine while the second force is applied to the flexible membrane; and determining whether the medical fluid cassette leaks based on a comparison of the first physical property and the second physical property.

In some aspects, method of detecting leaks in a disposable medical fluid cassette is provided. The medical fluid cassette includes a base and a flexible membrane attached to the base in such a way that the base and the flexible membrane cooperate to at least partially form a fluid passageway having fluid inlet ports and fluid outlet ports that provide communication between the fluid passageway and an exterior of the medical fluid cassette. The method includes applying a first force to the base; applying a second force to the membrane; closing the fluid inlet ports and the fluid outlet ports; measuring a first physical property of a system that includes the medical fluid cassette and a medical fluid pumping machine while the first force is applied to the base and the second force is applied to the membrane; removing the first force from the base; removing the second force from the flexible membrane; after measuring a first physical property and removing the first force and the second force, waiting a predetermined period of time; applying a third force to the base; applying a fourth force to the flexible membrane; measuring a second physical property of the system while the third force is applied to the base and the fourth force is applied to the membrane; and determining whether the medical fluid cassette leaks based on a comparison of the first physical property and the second physical property.

The methods may include one or more of the following additional steps or features: The first physical property comprises a first pressure within the medical fluid cassette and the second physical property comprises a second pressure within the medical fluid cassette. The medical fluid cassette is determined to have a leak if the second pressure is greater than the first pressure, and a difference between the second pressure and the first pressure is at least a given difference value. The medical fluid cassette is determined to have a leak if the second pressure is less than the first pressure, and a difference between the first pressure and the second pressure is at least a given difference value. The medical fluid pumping machine comprises a piston configured to be advanced against and withdrawn from the flexible membrane, applying the first force to the flexible membrane comprises advancing the piston against the flexible membrane until a given pressure within the medical fluid cassette is achieved, applying the second force to the flexible membrane comprises advancing the piston against the flexible membrane until the given pressure within the medical fluid cassette is achieved, the first physical property comprises a first position of the piston corresponding to the position of the piston when the given pressure is achieved while applying the first force, and the second physical property comprises a second position of the piston corresponding to the position of the piston when the given pressure is achieved while applying the second force. The comparison of the first physical property and the second physical property comprises calculating a difference between the first position and the second position. The first force is the same as the second force.

The methods may also include one or more of the following additional steps or features: The medical fluid cassette includes fluid inlet ports and fluid outlet ports that provide communication between the fluid passageway and an exterior of the medical fluid cassette, and applying the first force is performed with the fluid inlet ports and fluid outlet ports open. Before before removing the first force from the flexible membrane, the fluid inlet ports and fluid outlet ports are closed. The medical fluid cassette includes fluid inlet ports and fluid outlet ports that provide communication between the fluid passageway and an exterior of the medical fluid cassette, and applying the first force is performed with the fluid inlet ports and fluid outlet ports closed. The method further includes waiting for a given period of time to pass between removing the first force from the flexible membrane and applying the second force to the flexible membrane. The given period of time is in a range of 15 seconds to 60 seconds. The given period of time is in a range of 20 seconds to 30 seconds. The medical fluid cassette includes fluid inlet ports and fluid outlet ports that provide communication between the fluid passageway and an exterior of the medical fluid cassette, and between applying the first force to the flexible membrane and measuring the first physical property of the system, the method comprises closing the fluid inlet ports and fluid outlet ports such that fluid is trapped within the medical fluid cassette. The method includes applying a vacuum to an outer surface of the flexible membrane between removing the first force from the membrane and applying the second force to the membrane. The medical fluid cassette includes fluid inlet ports and fluid outlet ports that provide communication between the fluid passageway and an exterior of the medical fluid cassette, and before applying the first force to the flexible membrane, the method comprises closing the fluid inlet ports and fluid outlet ports such that fluid is trapped within the medical fluid cassette. Between closing the fluid inlet ports and fluid outlet ports such that fluid is trapped within the medical fluid cassette and applying the first force to the flexible membrane, the fluid within the cassette is redistributed. Applying the first force to the flexible membrane comprises applying the first force until at least a portion of the flexible membrane contacts the base. The medical fluid pumping machine comprises a piston, and applying the first force to the flexible membrane comprises advancing the piston toward the cassette to a predetermined position in a manner such that the space between the flexible membrane and the base comprises a predetermined. Applying the second force to the flexible membrane comprises advancing the piston to a position corresponding to the first physical property. The method includes applying a vacuum to an outer surface of the flexible membrane between removing the first force from the membrane and applying the second force to the membrane.

In some aspects, a medical fluid pumping machine is configured to receive a disposable medical fluid cassette. The medical fluid cassette includes a base and a flexible membrane attached to the base in such a way that the base and the flexible membrane cooperate to at least partially form a fluid passageway. The medical fluid pumping machine includes a compartment that receives the medical fluid cassette and a pressure applicator configured to apply a force to the medical fluid cassette when the medical fluid cassette is disposed within the compartment. The medical fluid pumping machine also includes a processer that is configured to: control the pressure applicator in such a way that a first force is applied to the flexible membrane when the medical fluid cassette is disposed within the compartment; measure a first physical property of a system that includes the medical fluid pumping machine with the medical fluid cassette disposed within the compartment while the first force is applied to the flexible membrane; control the pressure applicator in such a way that the first force is removed from the flexible membrane when the medical fluid cassette is disposed within the compartment; control the pressure applicator in such a way that a second force is applied to the flexible membrane when the medical fluid cassette is disposed within the compartment; measure a second physical property of the system that includes the medical fluid pumping machine with the medical fluid cassette disposed within the compartment while the second force is applied to the flexible membrane; and determine whether the medical fluid cassette leaks based on a comparison of the first physical property and the second physical property.

In some aspects, a medical fluid pumping machine is configured to receive a disposable medical fluid cassette. The medical fluid cassette includes a base and a flexible membrane attached to the base in such a way that the base and the flexible membrane cooperate to at least partially form a fluid passageway having fluid inlet ports and fluid outlet ports that provide communication between the fluid passageway and an exterior of the medical fluid cassette. The medical fluid pumping machine includes a compartment that receives the medical fluid cassette, a piston disposed within the compartment and configured to apply a force to the flexible membrane when the medical fluid cassette is disposed within the compartment, an inflatable pad disposed in the compartment between the base and a surface of the compartment, the inflatable bladder configured to apply a force to the base when the medical fluid cassette is disposed within the compartment, a clamp configured to close the fluid inlet ports and fluid outlet ports when the medical fluid cassette is disposed within the compartment, and a processer. The processor is configured to control the piston in such a way that a first force is applied to the flexible membrane when the medical fluid cassette is disposed within the compartment; control the inflatable pad in such a way that a second force is applied to the base when the medical fluid cassette is disposed within the compartment; control the clamp in such a way that the fluid inlet ports and fluid outlet ports are closed; measure a first physical property of a system that includes the medical fluid pumping machine with the medical fluid cassette disposed within the compartment while the first force is applied to the flexible membrane and the second force is applied to the base; control the piston in such a way that the first force is removed from the flexible membrane when the medical fluid cassette is disposed within the compartment; control the inflatable pad in such a way that the second force is removed from the base when the medical fluid cassette is disposed within the compartment; control the piston in such a way that a third force is applied to the flexible membrane when the medical fluid cassette is disposed within the compartment; control the inflatable pad in such a way that a fourth force is applied to the base when the medical fluid cassette is disposed within the compartment; measure a second physical property of the system that includes the medical fluid pumping machine with the medical fluid cassette disposed within the compartment while the third force is applied to the flexible membrane and the fourth force is applied to the base; and determine whether the medical fluid cassette leaks based on a comparison of the first physical property and the second physical property.

The medical fluid pumping machines may include one or more of the following features: The machine includes a vacuum source controllable by the processor and disposed within the compartment in a manner such that when activated while the medical fluid cassette is within the compartment, the vacuum source can apply a force to the flexible membrane, and the processor is configured to change a spacing between the flexible membrane and the base by activating the vacuum source. The processor is configured to change the spacing after controlling the pressure applicator in such a way that the first force is removed from the flexible membrane and before controlling the pressure applicator in such a way that the second force is applied to the flexible membrane. The vacuum source can apply a force to an outer surface of the flexible membrane. The machine includes a door that is configured to selectively close the compartment and retain the medical fluid cassette within the compartment, and an inflatable bladder disposed on an inside surface of the door and configured such that when inflated while the medical fluid cassette is within the compartment, the inflatable bladder is configured to compress the medical fluid cassette, and when deflated while the medical fluid cassette is within the compartment, the inflatable bladder is configured to contract against the inside surface of the door and generate a space between the inflatable bladder and the medical fluid cassette. The processer is configured to deflate the door bladder between controlling the pressure applicator in such a way that the first force is removed from the flexible membrane and controlling the pressure applicator in such a way that the second force is applied to the flexible membrane. Controlling the pressure applicator in such a way that the first force is applied to the flexible membrane comprises controlling the pressure applicator in such a way that the flexible membrane is compressed against the base. The pressure applicator comprises a piston configured to be advanced into and retracted from the compartment. The medical fluid cassette includes fluid inlet ports and fluid outlet ports that provide communication between the fluid passageway and an exterior of the medical fluid cassette, and controlling the pressure applicator in such a way that the first force is applied to the flexible membrane is performed with the fluid inlet ports and fluid outlet ports open. The medical fluid cassette includes fluid inlet ports and fluid outlet ports that provide communication between the fluid passageway and an exterior of the medical fluid cassette, and the processer is configured to close the fluid inlet ports and fluid outlet ports after controlling the pressure applicator in such a way that the first force is applied to the flexible membrane and before measuring the first pressure within the medical fluid cassette. The medical fluid cassette includes fluid inlet ports and fluid outlet ports that provide communication between the fluid passageway and an exterior of the medical fluid cassette, and controlling the pressure applicator in such a way that the first force is applied to the flexible membrane is performed with the fluid inlet ports and fluid outlet ports closed.

Implementations can include one or more of the following advantages.

In some implementations, a method of determining whether a medical fluid cassette (e.g., a PD fluid cassette) is leaking includes applying a force to the medical fluid cassette, measuring a first pressure of the medical fluid cassette, and then withdrawing the applied force from the medical fluid cassette. After a predetermined period of time, a force is applied to the medical fluid cassette, and a second pressure of the medical fluid cassette is measured. Based on a comparison of the first and second pressure measurements, it can be determined whether a leak in the flexible membrane of the medical fluid cassette exists. This method is advantageous over some conventional leak detection methods since the applied force is withdrawn from the medical fluid cassette between pressure measurements. In particular, for instances where the force is applied to a medical fluid cassette using pistons of a medical fluid pumping machine (e.g. a PD cycler) and a leak is located in the medical fluid cassette membrane in the vicinity of the pump chambers, particularly in the center of the pump chambers, the piston itself may obstruct the leak and provide a false confidence in membrane integrity during tests performed using a continuous applied force. By removing the applied force (for example, by retracting the pistons) between pressure measurements, the accuracy of leak detection measurements is improved since membrane leaks in the vicinity of the applied force not obstructed, permitting detection of leaks in the vicinity of the applied force (for example, in the membrane overlying the pump chambers).

In some implementations, a "dry" method of detecting leaks in a disposable medical fluid cassette is provided. For example, prior to performing peritoneal dialysis, the method is performed using air (rather than dialysate or other liquid) as a test fluid to determine whether a leak exists in a PD fluid cassette. Since the method includes testing the PD fluid cassette in a PD cycler prior to treatment, leaks are detected prior to initiating treatment cycles and can thus be remediated more conveniently than if detected during a treatment cycle. In addition, since air is used as the test fluid, the dialysis machine is protected from damage caused by leaks in the cassette. If a leak is detected in the cassette, there is no need to throw away any dialysate or to disinfect any portion of the apparatus. Moreover, if a leak is detected, liquid is prevented from entering the mechanical and pneumatic systems of the PD cycler.

In some implementations, the dialysis machine, upon detecting a leak, can alert the user to take remedial action such as replacing the cassette with a different cassette before permanent damage to the dialysis machine or to certain critical components of the dialysis machine occurs.

Other aspects, features, and advantages will be apparent from the description and drawings, and from the claims.

DETAILED DESCRIPTION

In general, this disclosure relates to methods of detecting leaks in medical fluid cassettes, and medical fluid pumping machines equipped to perform the methods. The leak detection methods include placing a medical fluid cassette (e.g., a PD fluid cassette) into a medical fluid pumping machine (e.g., a PD cycler), using the pistons of the PD cycler to apply a perturbation (e.g., a force) to the cassette, and measuring a physical property of the cassette-PD cycler system while the force is applied. The force is removed from the cassette, and, following a brief waiting period, the pistons of the PD cycler are again used to apply a force to the cassette. At this time, a second measurement of the physical property is made while the force is applied to the cassette. The PD cycler determines whether the cassette leaks based on a comparison of the first physical property and the second physical property. By removing the force from the cassette (e.g, retracting the pistons of the PD cycler away from the cassette) during implementation of the method, leaks in the cassette in the vicinity of the applied force become unobstructed, whereby leak detection measurements more accurately reflect the condition of the cassette than some methods in which the force is applied continuously throughout the test method. In response to detecting a leak, action can be taken by the user and/or by the medical fluid pumping machine itself to reduce the likelihood of or prevent permanent damage to the medical fluid pumping machine or to certain components within the medical fluid pumping machine.

Figure 1:
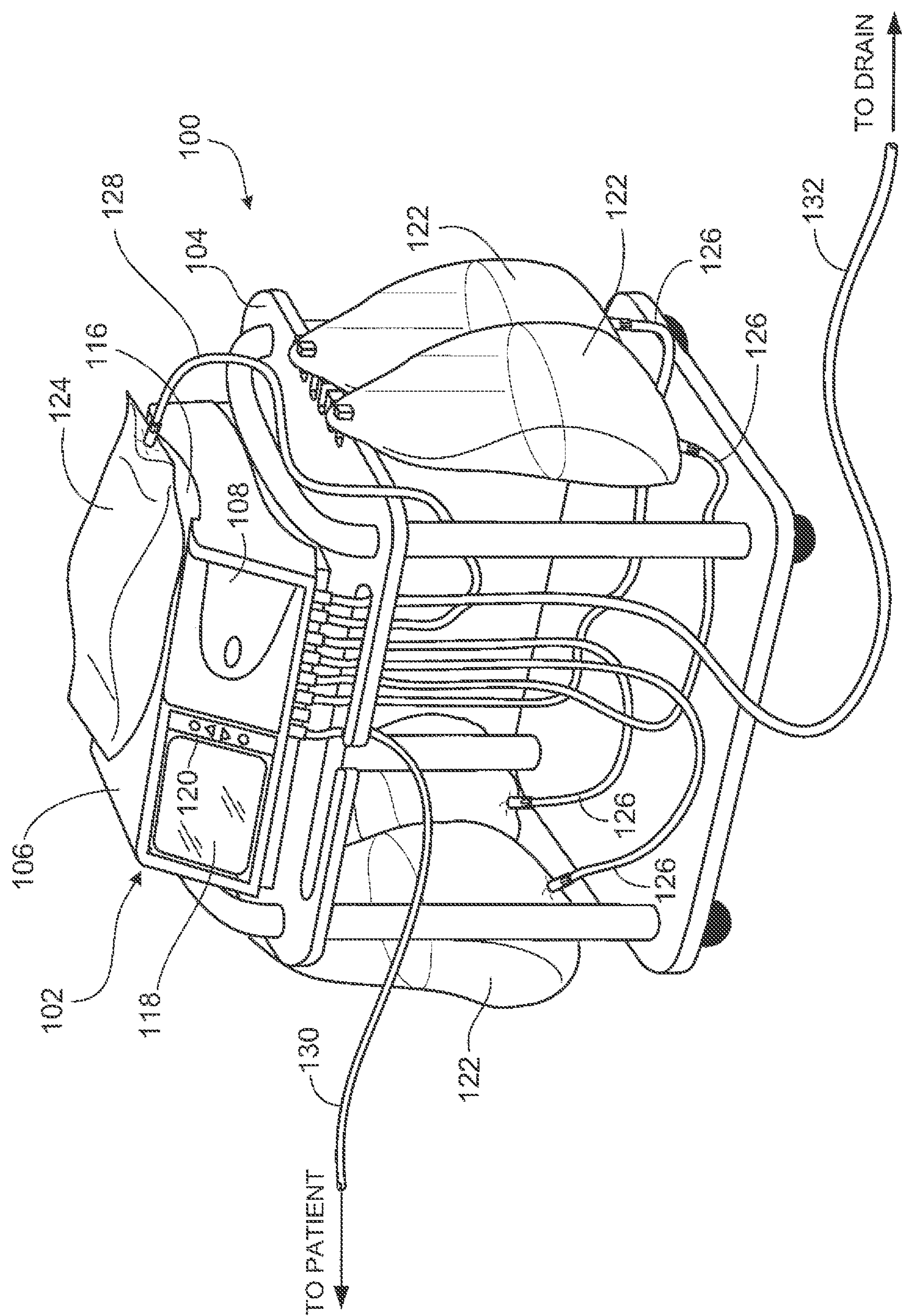
FIG. 1 is a perspective view of a peritoneal dialysis ("PD") system that includes a PD cycler positioned atop a portable cart.
Figure 2:
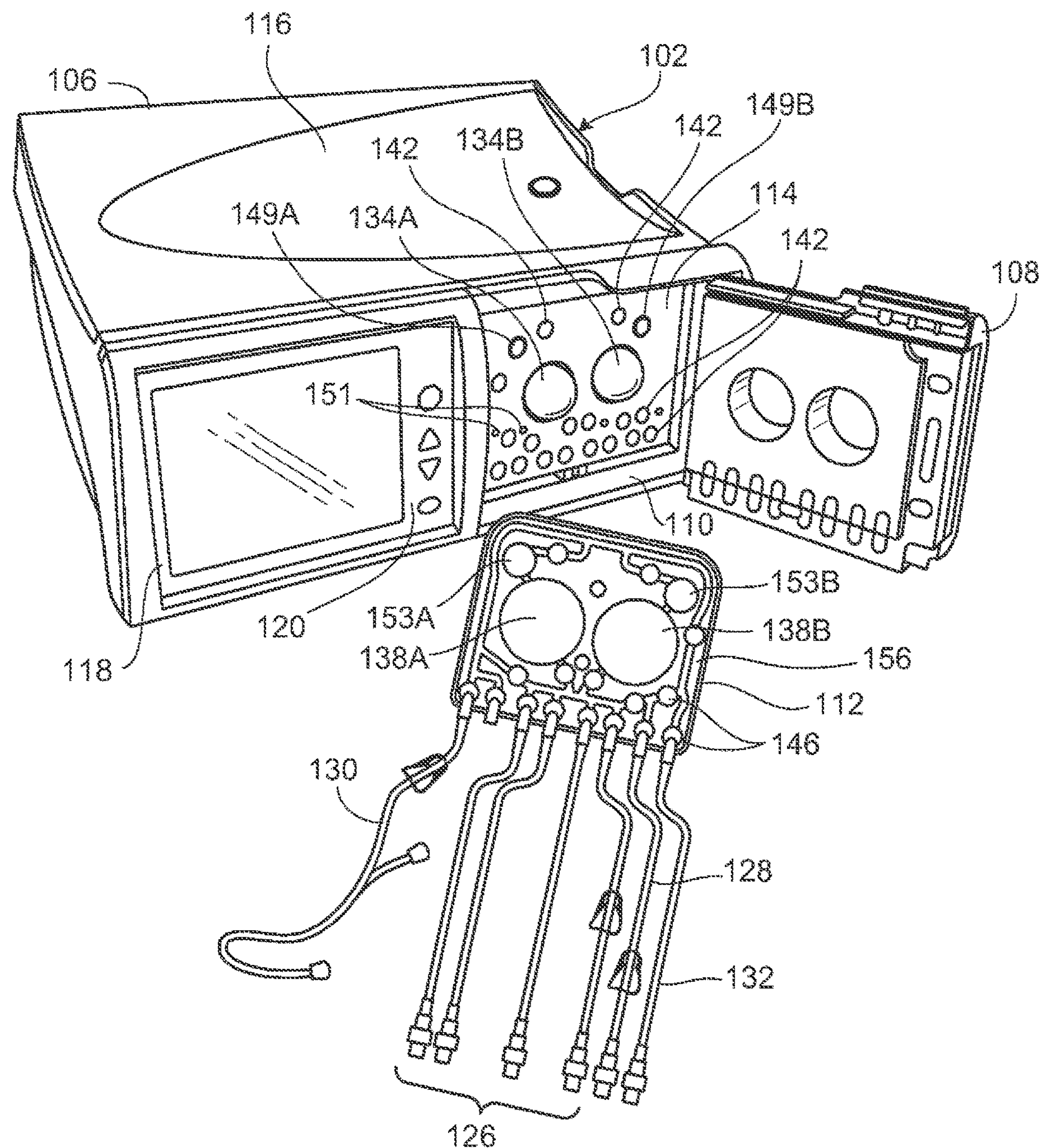
FIG. 2 is a perspective view of the PD cycler and a PD cassette of the PD system of FIG. 1, with a door of the PD cycler in the open position to show the inner surfaces of the PD cycler that interface with the PD cassette during use.

Referring to FIG. 1, a peritoneal dialysis ("PD") system 100 includes a PD cycler (also referred to as a PD machine) 102, and a disposable PD fluid cassette 112 disposed within the PD cycler 102. The PD cycler 102 is seated on a cart 104. Referring also to FIG. 2, the PD cycler 102 includes a housing 106, a door 108, and a cassette interface 110 that mates with the cassette 112 when the cassette 112 is disposed within a cassette compartment 114 formed between the cassette interface 110 and the door 108. As discussed below, the cassette 112 includes a flexible membrane secured to a rigid base 156 to form pump chambers 138A, 138B and fluid passages through which dialysate passes during use. A heater tray 116 is positioned on top of the housing 106. The heater tray 116 is sized and shaped to accommodate a bag of dialysate (e.g., a 5 liter bag of dialysate). The PD cycler 102 also includes a touch screen 118 and additional control buttons 120 that can be operated by a user (e.g., a patient) to allow, for example, set-up, initiation, and/or termination of a PD treatment.

Dialysate bags 122 are suspended from fingers on the sides of the cart 104, and a heater bag 124 is positioned on the heater tray 116. The dialysate bags 122 and the heater bag 124 are connected to the cassette 112 via dialysate bag lines 126 and a heater bag line 128, respectively. The dialysate bag lines 126 can be used to pass dialysate from the dialysate bags 122 to the cassette 112 during use, and the heater bag line 128 can be used to pass dialysate back and forth between the cassette 112 and the heater bag 124 during use. In addition, a patient line 130 and a drain line 132 are connected to the cassette 112. The patient line 130 can be connected to a patient's abdomen via a catheter and can be used to pass dialysate back and forth between the cassette 112 and the patient during use. The drain line 132 can be connected to a drain or drain receptacle and can be used to pass dialysate from the cassette 112 to the drain or drain receptacle during use.

Figure 3:
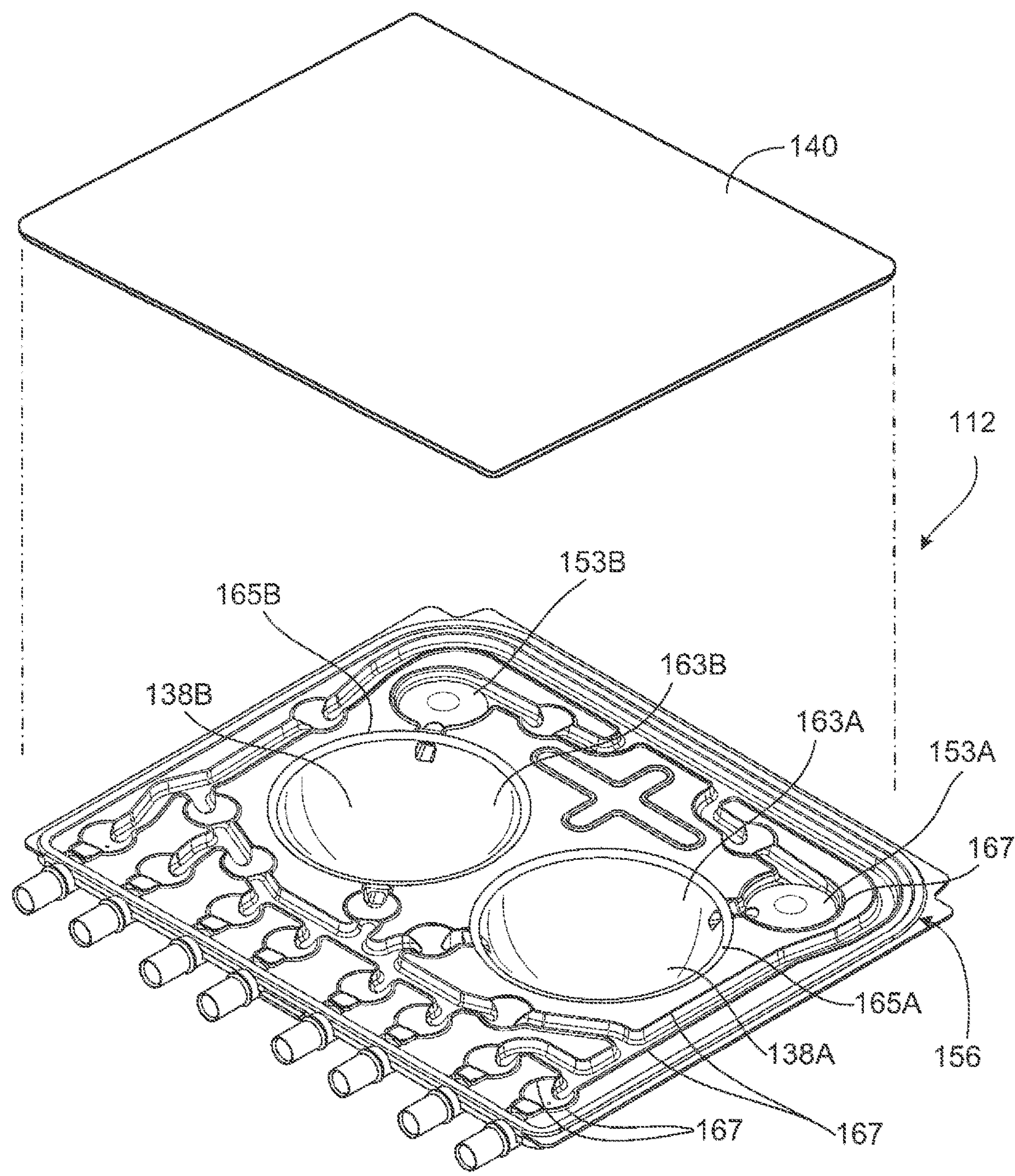
FIG. 3 is an exploded, perspective view of the PD cassette of the PD system of FIG. 1.

First the cassette 112 will be described. That discussion will be followed by a description of the PD cycler 102. FIG. 3 is an exploded, perspective view of the cassette 112. As shown in FIG. 3, the cassette 112 includes the tray-like rigid base 156 and a flexible membrane 140, which is attached to the periphery of the base 156 when the cassette 112 is fully assembled. The base 156 includes recessed regions 163A, 163B that partially define the pump chambers 138A, 138B of the cassette 112. Raised ridges 165A, 165B extend from a planar surface of the base 156 around each of the recessed regions 163A, 163B and extend towards and into contact with the inner surface of the flexible membrane 140 when the cassette 112 is compressed between the door 108 and the cassette interface 110 of the PD cycler 102. In addition to the raised ridges 165A, 165B surrounding the recessed regions 163A, 163B, a series of raised ridges 167 extend from the planar surface of the base 156 towards and into contact with the inner surface of the flexible membrane 140 when the cassette 112 is compressed between the door 108 and the cassette interface 110 of the PD cycler 102.

Figure 4:
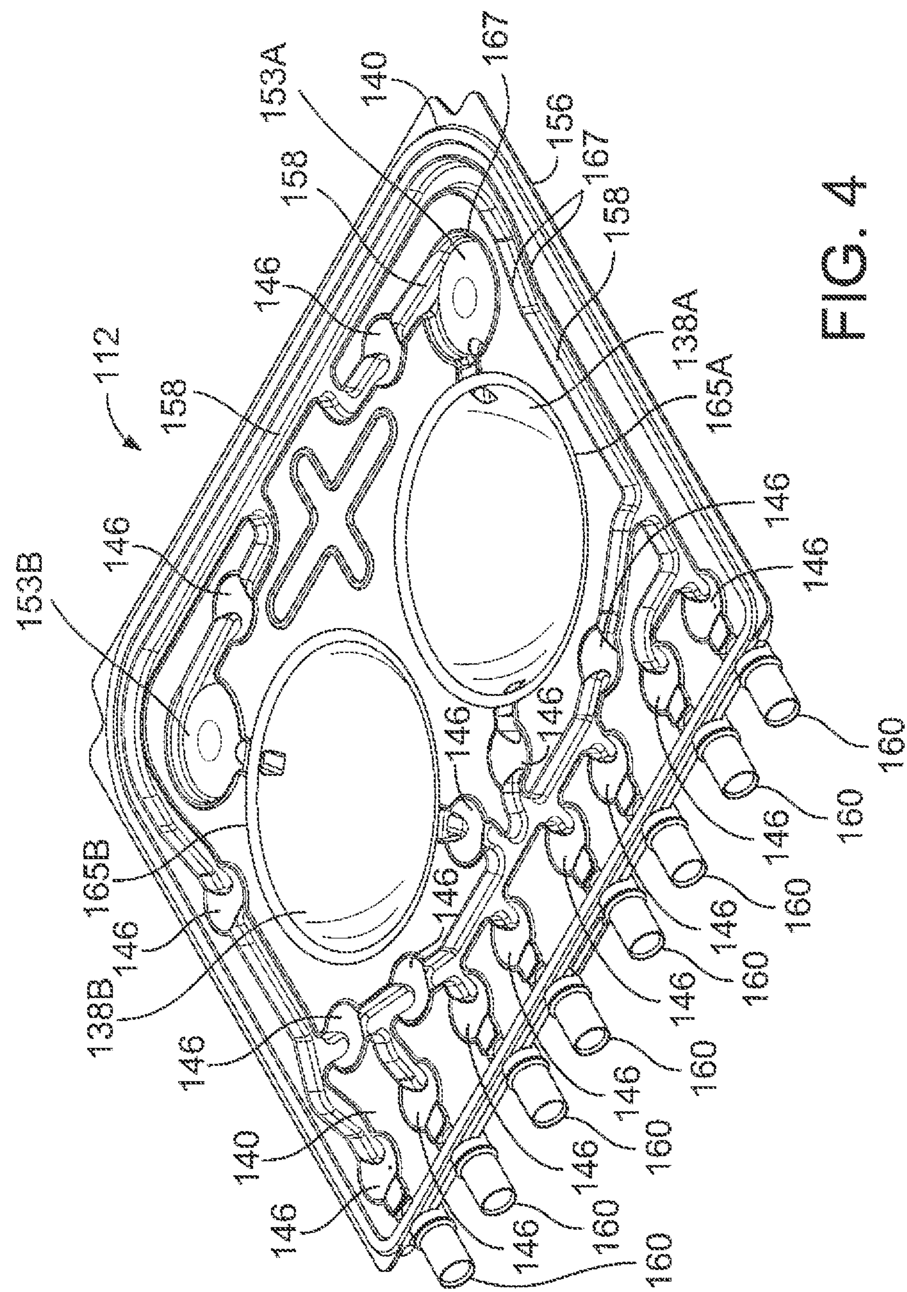
FIG. 4 is a perspective view of the assembled PD cassette of FIG. 3. A rigid base of the cassette is visible through a clear flexible membrane that is attached to the base.

FIG. 4 is a perspective view of the assembled cassette 112. The features of the rigid base 156 are visible through the transparent flexible membrane 140. Referring to both FIGS. 3 and 4, the recessed regions 163A, 163B of the base 156 cooperate with the flexible membrane 140 to form the pump chambers 138A, 138B when the cassette 112 is compressed between the door 108 and the cassette interface 110 of the PD cycler 102 resulting in the flexible membrane 140 being pressed against the raised ridges 165A, 165B of the base 156. In particular, the volumes between the membrane 140 and the hollow projections that form the recessed regions 163A, 163B of the base 156 serve as the pump chambers 138A, 138B. The membrane 140, when compressed against the base 156, similarly cooperates with the series of raised ridges 167 extending from the base 156 to form a series of fluid pathways 158 and to form multiple, depressible dome regions 146, which are widened portions (e.g., substantially circular widened portions) of the fluid pathways 158. The membrane 140, when compressed against the base 156, also cooperates with certain raised ridges 167 to form pressure sensor chambers 153A, 153B.

During use, liquid, such as dialysate, flows to and from the pump chambers 138A, 138B through the fluid pathways 158 and the dome regions 146. At each depressible dome region 146, the membrane 140 can be deflected to contact the planar surface of the base 156 from which the raised ridges 167 extend. Such contact can substantially impede (e.g., prevent) the flow of dialysate along the region of the pathway 158 associated with that dome region 146. Thus, as described in further detail below, the flow of dialysate through the cassette 112 can be controlled through the selective depression of the depressible dome regions 146 by selectively inflating mating inflatable members on the cassette interface 110 of the PD cycler 102.

As noted above, the membrane 140 is attached (e.g., adhesively and/or thermally bonded) to the periphery of the base 156. The portion of the membrane 140 overlying the central portion of the base 156 is not necessarily attached to the base 156. Rather, this portion of the membrane 140 may sit loosely atop the raised ridges 165A, 165B, 167 extending from the planar surface of the base 156. The thickness and material(s) of the membrane 140 are selected so that the membrane 140 has sufficient flexibility to flex toward the base 156 in response to the force applied to the membrane 140 by piston heads and inflatable members of the PD cycler 102, which will be described in greater detail below. In certain implementations, the membrane 140 is about 0.100 micron to about 0.150 micron in thickness. However, various other thicknesses may be sufficient depending on the type of material used to form the membrane 140.

Any of various different medical grade materials that permit the membrane 140 to deflect in response to movement of the piston heads and inflation of the inflatable members of the PD cycler 102 without tearing can be used to form the membrane 140. In some implementations, the membrane 140 includes a three-layer laminate. In certain implementations, for example, inner and outer layers of the laminate are formed of a compound that is made up of 60 percent Septon® 8004 thermoplastic rubber (i.e., hydrogenated styrenic block copolymer) and 40 percent ethylene, and a middle layer is formed of a compound that is made up of 25 percent Tuftec® H1062(SEBS: hydrogenated styrenic thermoplastic elastomer), 40 percent Engage® 8003 polyolefin elastomer (ethylene octene copolymer), and 35 percent Septon® 8004 thermoplastic rubber (i.e., hydrogenated styrenic block copolymer). The membrane 140 can alternatively include more or fewer layers and/or can be formed of different materials.

As shown in FIG. 4, fluid line connectors 160 are positioned along the bottom edge of the cassette 112. The fluid pathways 158 in the cassette 112 lead from the pumping chambers 138A, 138B to the various connectors 160. The connectors 160 are configured to receive fittings on the ends of the dialysate bag lines 126, the heater bag line 128, the patient line 130, and the drain line 132. One end of the fitting can be inserted into and bonded to its respective line and the other end can be inserted into and bonded to its associated connector 160. By permitting the dialysate bag lines 126, the heater bag line 128, the patient line 130, and the drain line 132 to be connected to the cassette, as shown in FIGS. 1 and 2, the connectors 160 allow dialysate to be pumped into and out of the cassette 112 during use.

Figure 5:
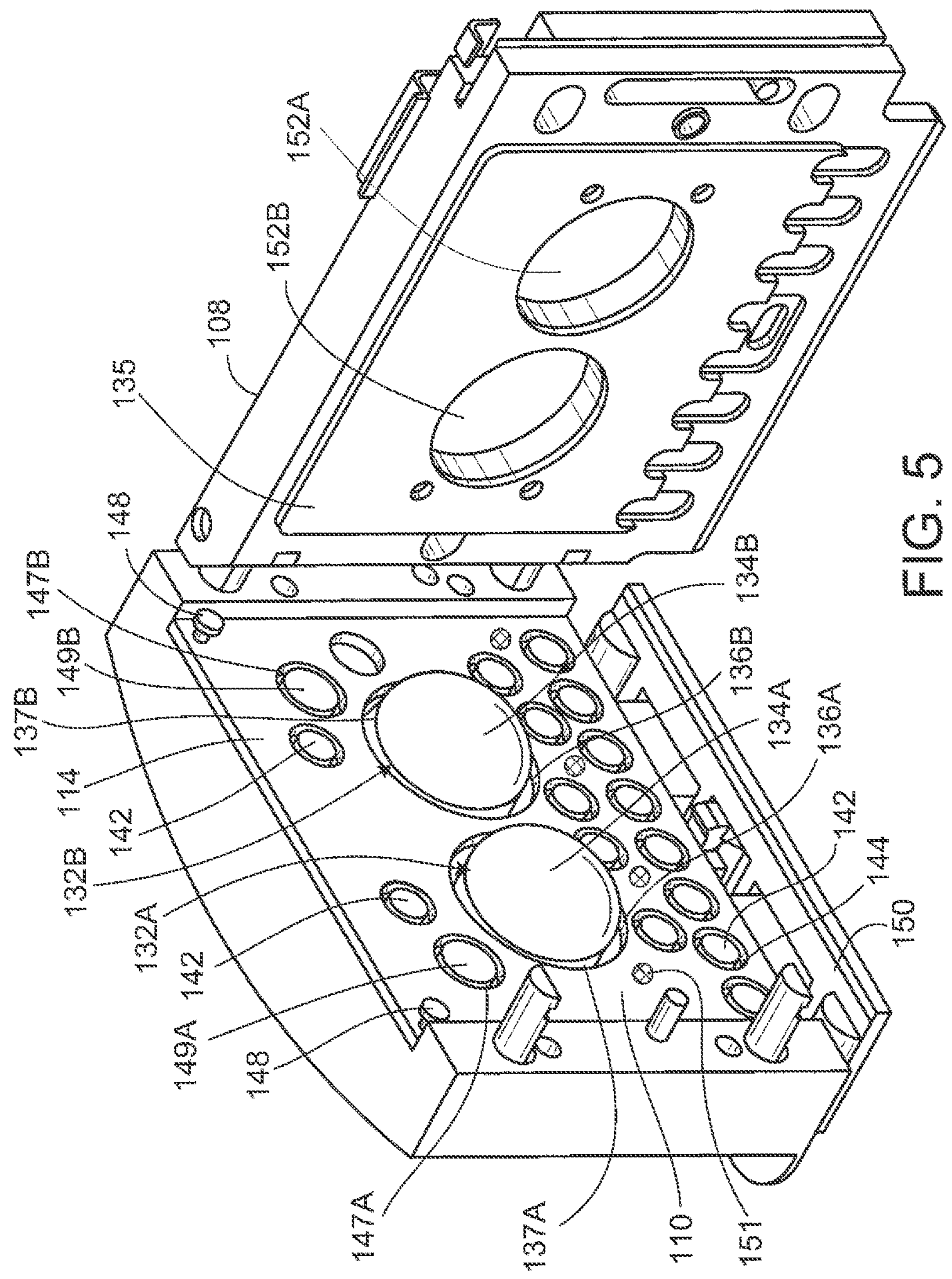
FIG. 5 is a perspective view of an open cassette compartment of the PD cycler of FIG. 1.

FIG. 5 shows a detailed view of the cassette interface 110 and the door 108 of the PD cycler 102. As shown, the PD cycler 102 includes pistons 132A, 132B with substantially hemispherical piston heads 134A, 134B that can be axially moved within piston access ports 136A, 136B formed in the cassette interface 110. The piston access ports 136A, 136B form annular passages 137A, 137B that surround the piston heads 134A, 134B and are in fluid communication with portions of the cassette membrane 140 overlying pump chambers 138A, 138B when the cassette 112 is disposed in the cassette compartment 114 of the PD cycler 102. As a result, vacuum pressure applied to the annular passages 137A, 137B during use of the PD cycler 102 can be used to draw the membrane 140 of the cassette 112 against the piston heads 134A, 134B.

Still referring to FIG. 5, the pistons 132A, 132B are coupled to motors that can be operated to move the piston heads 134A, 134B axially inward and outward within the piston access ports 136A, 136B. When the cassette 112 is positioned within the cassette compartment 114 with the door 108 closed, the piston heads 134A, 134B of the PD cycler 102 align with the pump chambers 138A, 138B of the cassette 112. As a result, the piston heads 134A, 134B can be moved in the direction of the cassette 112 to force the membrane 140 of the cassette 112 toward the rigid base 156, causing the volume defined by the pump chambers 138A, 138B to decrease and forcing dialysate out of the pump chambers 138A, 138B. The piston heads 134A, 134B can also be retracted away from the base 156 of the cassette 112. Portions of the cassette membrane 140 overlying the pump chambers 138A, 138B are drawn toward the piston heads 134A, 134B with vacuum force as the pistons heads 134A, 134B are retracted. In particular, the annular passages 137A, 137B surrounding the piston heads 134A, 134B (i.e., the portions of the piston access ports 136A, 136B that surround the piston heads 134A, 134B) can be used to apply a vacuum force to those portions of the membrane 140 overlying the pump chambers 138A, 138B. The piston access ports 136A, 136B are connected to a vacuum source (e.g., an air pump or vacuum tank) to allow the vacuum pressure to be applied to the membrane 140 of the cassette 112 via the annular passages 137A, 137B. As a result, the volume defined by the pump chambers 138A, 138B increases and dialysate is drawn into the pump chambers 138A, 138B as the piston heads 134A, 134B retract together with respective portions of the cassette membrane 140.

As shown in FIG. 5, the PD cycler 102 also includes multiple inflatable members 142 positioned within inflatable member access ports 144 in the cassette interface 110. The inflatable members 142 align with the depressible dome regions 146 of the cassette 112 when the cassette 112 is positioned within the cassette compartment 114. The inflatable members 142 are connected to fluid lines that act as conduits for applying positive pressure and/or vacuum pressure to the inflatable members 142 such that the inflatable members 142 can be inflated and deflated during use. While not all of the inflatable members 142 are labeled in FIG. 5, it should be understood that the PD cycler 102 includes an inflatable member associated with each of the depressible dome regions 146 of the cassette 112 (shown in FIG. 4). The inflatable members 142 act as valves to direct dialysate through the cassette 112 in a desired manner during use. In particular, the inflatable members 142 bulge outward beyond the surface of the cassette interface 110 and into contact with the depressible dome regions 146 of the cassette 112 when inflated, and retract into the inflatable member access ports 144 and out of contact with the cassette 112 when deflated. By inflating certain inflatable members 142 to depress their associated dome regions 146 on the cassette 112, certain fluid flow paths within the cassette 112 can be blocked off. Thus, dialysate can be pumped through the cassette 112 by actuating the piston heads 134A, 134B, and can be guided along desired flow paths within the cassette 112 by selectively inflating and deflating the inflatable members 142.

Still referring to FIG. 5, the cassette interface 110 also includes vacuum ports 151 that are connected to vacuum lines positioned within the housing of the PD cycler 102. The vacuum ports 151 allow vacuum pressure to be applied to the cassette membrane 140 when the cassette 112 is positioned adjacent to the cassette interface 110. Applying vacuum pressure to the membrane 140 through the vacuum ports 151 draws the membrane 140 toward the cassette interface 110, thereby forming a seal between the cassette interface 110 and the membrane 140.

The cassette interface 110 also includes pressure sensors 149A, 149B. These sensors can, for example, be solid state silicon diaphragm infusion pump force/pressure transducers. An example of such a transducer is Model 1865 made by Sensym Foxboro ICT. Output signals generated by the pressure sensors 149A, 149B are transmitted to a control unit (e.g., processor) 1090 (shown in FIG. 7) of the PD cycler 102 via a wired or wireless connection. When the cassette 112 is inserted into the cassette compartment 114, the pressure sensing chambers 153A, 153B (shown in FIG. 4) of the cassette 112 line up and are in contact with the pressure sensors 149A, 149B. These pressure sensing chambers 153A and 153B are connected directly to the pump chambers 138A and 138B, respectively, of the cassette 112 such that when dialysate moves into and out of the pump chambers 138A, 138B, the pressure sensors 149A, 149B can measure the pressure of the dialysate passing through the pressure sensing chambers 153A, 153B, and can thus detect the pressure of the dialysate in the associated pump chamber 138A, 138B. The cassette membrane 140 is drawn against the pressure sensors 149A, 149B using vacuum pressure. In particular, annular passages 147A, 147B that surround the pressure sensors 149A, 149B allow vacuum pressure to be applied to the cassette membrane 140. Drawing the cassette membrane 140 close to the pressure sensors 149A, 149B can improve the accuracy of the pressure readings detected by those sensors.

The door 108, as shown in FIG. 5, defines recesses 152A, 152B that substantially align with the piston heads 134A, 134B when the door 108 is in the closed position. When the cassette 112 is positioned within the cassette compartment 114, hollow projections that form the recessed regions 163A, 163B in the base 156 of the cassette 112 and cooperate with the membrane 140 to form the pump chambers 138A, 138B fit within the recesses 152A, 152B in the door 108. An inflatable pad 135 in the door 108 can be inflated during use to compress the cassette 112 between the door 108 and the cassette interface 110. With the pad 135 inflated, the portions of the door 108 forming the recesses 152A, 152B support the hollow projections of the base 156 of the cassette 112 and the planar surface of the door 108 supports the other regions of the base 156 of the cassette 112. The door 108 can counteract the forces applied by the piston heads 134A, 134B and the inflatable members 142 and thus allows the piston heads 134A, 134B to depress the portions of the cassette membrane 140 overlying the pump chambers 138A, 138B and similarly allows the inflatable members 142 to actuate the depressible dome regions 146 on the cassette 112.

The PD cycler also includes a safety clamp 150, which serves to close all inlets to and outlets from the cassette, for example, in the case of a system error. As seen in FIG. 5, the safety clamp 150 is a bar arranged below the cassette compartment. The safety clamp 150 is spring biased to a closed position in which the bar is urged against an interior surface of the door 108. When in the closed position, the safety clamp 150 extends across all of the lines 126, 128, 130, 132 connected to the cassette 112, whereby all lines 126, 128, 130, 132 extending from the cassette 112 are crimped closed. During normal operation, the safety clamp 150 is retracted away from the door 108 using pneumatic pistons operated by the pneumatic system, as discussed further below.

Figure 6:
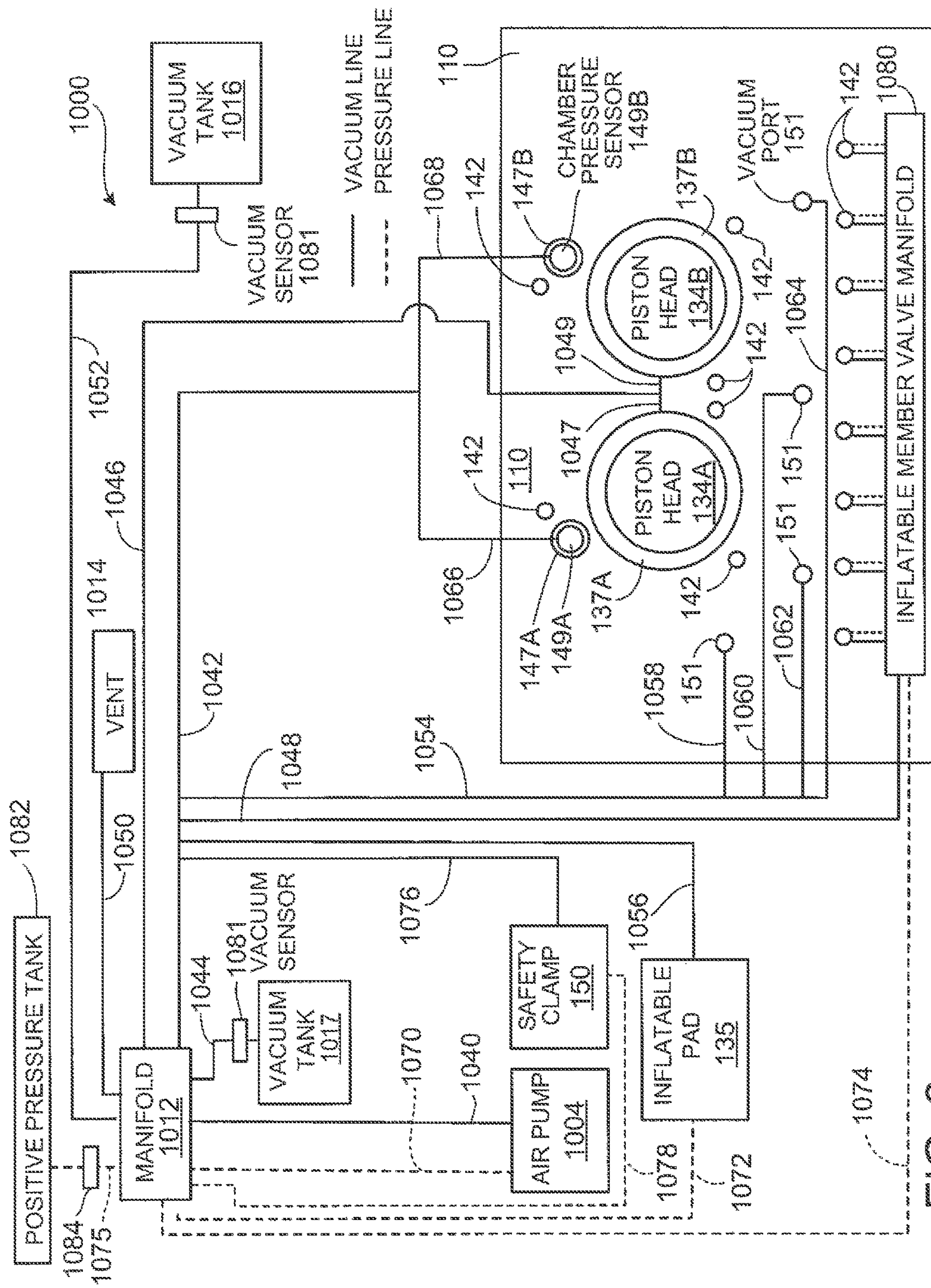
FIG. 6 is a schematic illustration of an air distribution system of the PD cycler of FIG. 1.

FIG. 6 is a schematic of an air distribution system 1000 of the PD cycler 102. The air distribution system 1000 includes an air pump 1004 that is configured to generate positive air pressure or negative (vacuum) air pressure and can be used to apply that positive pressure or vacuum pressure to the annular passages 137A, 137B surrounding the piston heads 134A, 134B, to the inflatable members 142, to the vacuum ports 151, and/or to the annular passages 147A, 147B surrounding the pressure sensors 149A, 149B. The air pump 1004 is connected via air lines or tubes 1040, 1070 to a valve manifold 1012. The air line 1040 is connected to a vacuum outlet port of the air pump 1004 to supply vacuum pressure to the manifold 1012, and the air line 1070 is connected to a positive pressure outlet port of the air pump 1004 to supply positive pressure to the manifold 1012. The air line 1070 and other air lines of the air distribution system 1000 that carry positive pressure air are shown in dashed lines in FIG. 6.

The manifold 1012 includes multiple valves that can be actuated to guide the positive and negative pressure received from the air pump 1004 in a desired manner through any of various different air lines 1042, 1046, 1050, 1072, 1074, 1075 and 1078 connected to the manifold 1012. The valves of the manifold 1012 can, for example, be solenoid valves that are controlled by the control unit (e.g., processor) 1090 (shown in FIG. 7) of the PD cycler 102.

An air line 1048 is connected via a T-connector to the air line 1042. An opposite end of the air line 1048 is connected to an inflatable member valve manifold 1080. The air line 1074 extending from the manifold 1012 is also connected to the inflatable member valve manifold 1080. Thus, positive air pressure can be carried from the air line 1042 to the inflatable member valve manifold 1080 via the air line 1048, and vacuum pressure can be carried from the manifold 1012 to the inflatable member valve manifold 1080 via the air line 1074.

Positive air pressure or vacuum pressure can be delivered to the inflatable members 142 via one or more lines that connect(s) each of the inflatable members 142 to the inflatable member valve manifold 1080. FIG. 6 shows a separate pressure line and vacuum line connected to each of the eight inflatable members 142 positioned along the bottom region of the cassette interface 110. It should be understood that similar lines connect each of the other inflatable members 142 to the inflatable member valve manifold 1080, but, for clarity, those lines are not illustrated in FIG. 6. Also, while each inflatable member 142 has been described as being connected to a separate pressure line and vacuum line, it should be understood that positive pressure and vacuum pressure could be distributed to each inflatable member 142 using only a single line connecting the inflatable member valve manifold 1080 to that inflatable member 142. The inflatable member valve manifold 1080, like the manifold 1012, includes multiple valves that can be selectively controlled by the control unit 1090 to apply vacuum pressure or positive air pressure to the various inflatable members 142. By controlling the pressure supplied to the inflatable valve numbers 142, each of the inflatable valve members 142 can be held in an inflated or a deflated state. As noted above, inflating and deflating the various inflatable members 142 can be used to control fluid flow through the cassette 112.

An air line 1054 is also connected via a T-connector to the air line 1042. Air lines 1058, 1060, 1062, and 1064 extend between the air line 1054 and the vacuum ports 151. Thus, air lines 1054, 1058, 1060, 1062, and 1064 can be used to supply vacuum pressure from the air line 1042 to the vacuum ports 151 formed in the cassette interface 110 of the PD cycler 102. The vacuum pressure applied to the vacuum ports 151 can be used to pull the membrane 140 of the cassette 112 against the cassette interface 110 of the PD cycler 102.

An end of the air line 1042 opposite the manifold 1012 is connected to air lines 1066, 1068 by a T-connector. The air lines 1066, 1068 are in fluid communication with the annular passages 147A, 147B surrounding chamber pressure sensors 149A, 149B. Supplying vacuum pressure to the annular passages 147A, 147B can help to ensure that the membrane 140 of the cassette 112 is pulled firmly against the pressure sensors 149A, 149B and can thus increase the accuracy of pressure measurements detected by those sensors.

An end of the air line 1046 opposite the manifold 1012 is connected to air lines 1047, 1049, which are in fluid communication with the annular passages 137A, 137B surrounding the piston heads 134A, 134B. As a result, vacuum pressure can be supplied to the annular passages 137A, 137B via the air lines 1046, 1047, and 1049. This vacuum pressure can help secure the membrane 140 of the cassette 112 to the piston heads 134A, 134B as the piston heads 134A, 134B are reciprocated during use.

The inflatable pad 135 located on the door 108 of the PD cycler 102 receives vacuum pressure via an air line 1056, which is connected via a T-connector to the air line 1042, and receives positive air pressure via an air line 1072, which is connected to the manifold 1012. Positive pressure can be selectively applied (i.e., by controlling the valves of the manifold 1012) to the inflatable pad 135 in order to inflate the inflatable pad 135. In order to deflate the inflated pad 135, the pressure is exhausted to atmosphere (i.e., by controlling the valves of the manifold 1012). The inflatable pad 135, as described above, can be used to compress the cassette 112 against the cassette interface 110 of the PD cycler 102, which can help to ensure that the membrane 140 of the cassette 112 is held firmly in contact with the various components exposed on the surface of the cassette interface 110 of the PD cycler 102 during use.

The safety clamp 150 located on the PD cycler 102 along a lower edge of the cassette compartment receives vacuum pressure via an air line 1076, which is connected via a T-connector to the air line 1042, and receives positive air pressure via an air line 1078, which is connected to the manifold 1012. Positive pressure can be selectively applied (i.e., by controlling the valves of the manifold 1012) to the safety clamp 150 in order to retract the safety clamp away from the door 108 against the biasing force of a bias spring (not shown). In order to actuate the safety clamp 150, the pressure is exhausted to atmosphere (i.e., by controlling the valves of the manifold 1012), permitting the bias spring to advance the safety clamp toward the door 108. The safety clamp 150, as described above, serves to close all inlets to and outlets from the cassette 112 in the case of a system error.

Still referring to FIG. 6, a vacuum tank 1016 is also connected to the valve manifold via the manifold 1012 and air line 1052. The vacuum tank 1016 contains a supply of air maintained at a negative pressure (e.g., at a pressure of about −150 mbar to about −200 mbar). During use, valves of the manifold 1012 can be operated in a manner to pull a vacuum on the annular passages 137A, 137B via the air lines 1046, 1047, 1049. The vacuum tank 1016 can be used as an alternative to or in addition to the air pump 1004 in order to supply vacuum pressure to the annular passages 137A, 137B. Typically, the air pump 1004 is simply used in an intermittent fashion to ensure that the vacuum tank 1016 is maintained at a desired negative pressure, and the vacuum tank is used to apply negative pressure to the annular passages 137A, 137B. A vacuum pressure of about −150 mbar to about −200 mbar is typically applied to the annular passages 137A, 137B and thus to the portions of the cassette membrane 140 positioned adjacent those annular passages 137A, 137B. By utilizing the vacuum tank 1016 as a supplement to or substitute for the air pump 1004 during use, the time period during which the air pump 1004 needs to be operated during use can be reduced. This can advantageously reduce the noise associated with operating the air pump 1004.

A vacuum tank 1017 is similarly connected to the valve manifold 1012 via an air line 1044. The vacuum tank 1017 can be operated in a manner similar to the vacuum tank 1016 to supply vacuum pressure to the inflatable members 142, the vacuum ports 151, and the annular passages 147A, 147B surrounding the pressure sensors 149A, 149B via the air lines 1042 and the various air lines connected to that air line 1042. A vacuum pressure of about −550 mbar can be applied to the inflatable members 142, the vacuum ports 151, and the annular passages 147A, 147B surrounding the pressure sensors 149A, 149B.

The air lines 1052 and 1044 that are connected to the vacuum tanks 1016 and 1017 are equipped with vacuum sensors 1081 that can detect vacuum pressure within those lines. Any of various different types of vacuum sensors capable of detecting the vacuum pressure within the air lines 1052, 1044 can be used. An example of a suitable vacuum sensor is the ASDX-15 force/pressure transducers available from Honeywell (Morristown, N.J.). Other suitable vacuum sensors, including the Sensor Technics RXUP015 and the All Sensors 15 PSI-Dx-4V-MINI, can alternatively or additionally be used.

In addition, a positive pressure tank 1082 is connected to the manifold 1012 via an air line 1075. The tank 1082 contains air that is positively pressurized. The air within the tank can, for example, be pressurized to a pressure of about 20 psi to about 60 psi (e.g., about 40 psi). The air line 1075 is equipped with a pressure sensor 1084 configured to measure the pressure of air within the line 1075. An example of a suitable pressure sensor is the ASDX-100 force/pressure transducers available from Honeywell (Morristown, N.J.). Other suitable pressure sensors, including the Sensor Technics RXUP0100 and the All Sensors 100 PSI-Dx-4V-MINI can alternatively or additionally be used.

During use, the manifold 1012 can be operated in a manner such that pressurized air is supplied from the positive pressure tank 1082 to the inflatable member valve manifold 1080 and/or to the inflatable pad 135. For example, by opening valves of the manifold 1012 associated with the air line 1075 and the air line 1074, positive pressure can be supplied from the positive pressure tank 1082 via the air line 1074 to the inflatable member valve manifold 1080. Similarly, by opening the valves of the manifold 1012 associated with the air line 1075 and the air line 1072, positive pressure can be supplied from the positive pressure tank 1082 via the air line 1072 to the inflatable pad 135 in the door 108 of the PD cycler 102. The positive pressure tank 1082 can be used instead of or in addition to the air pump 1004 for delivering positive pressure to the inflatable pad 135 and the inflatable member valve manifold 1080. As discussed above, by limiting operation of the air pump 1004, the noise level associated with operating the PD cycler 102 can advantageously be reduced.

A vent or muffler 1014 is connected to an air line 1050 extending from the manifold 1012. The vent 1014 can be used to vent air lines (e.g., positively pressurized air lines and/or negatively pressurized air lines) to atmosphere during use. This can help to regulate air pressures within the various air lines of the air distribution system 1000.

Figure 7:
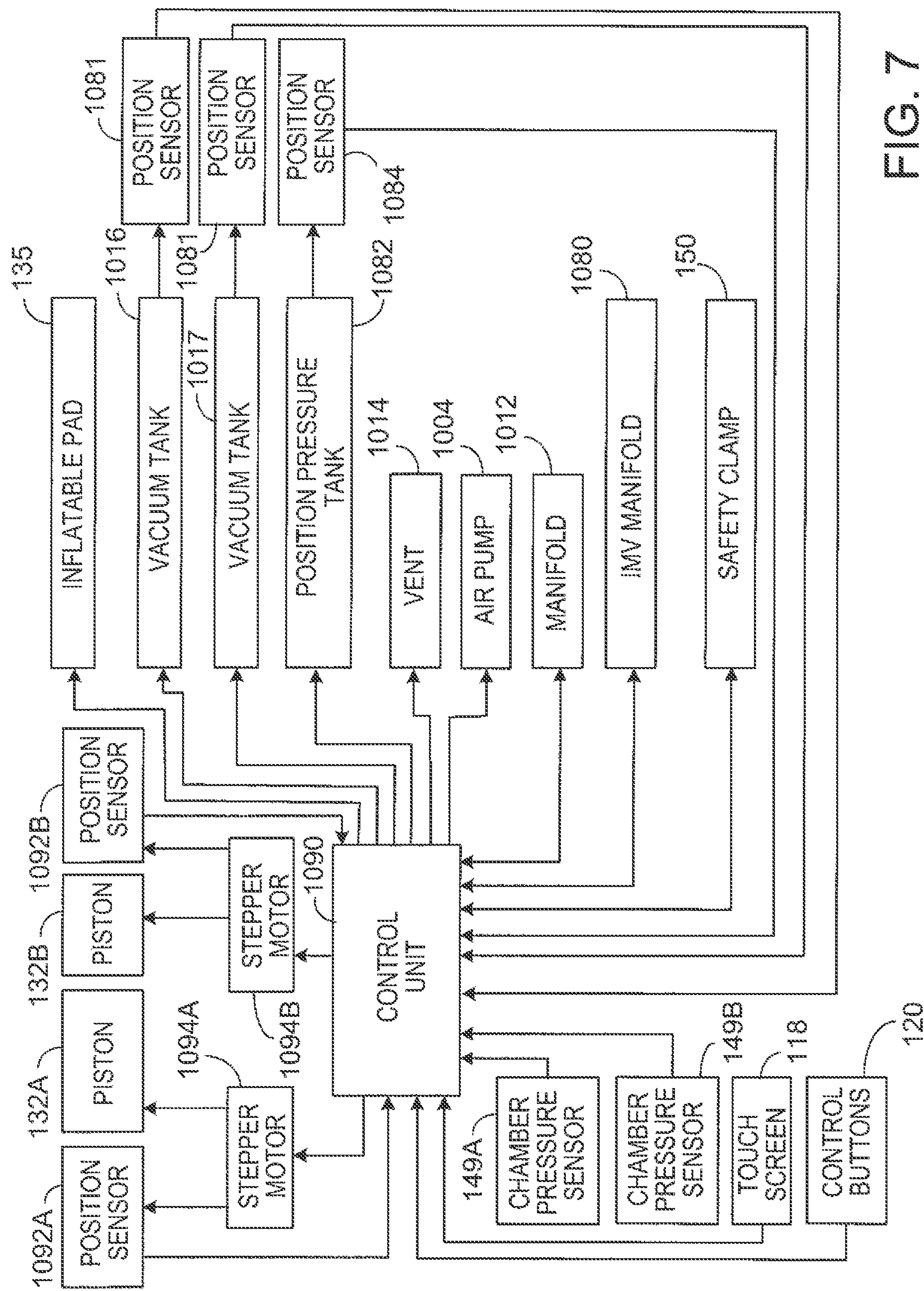
FIG. 7 is a schematic illustration of a control system of the PD cycler of FIG. 1.

Referring to FIG. 7, the control system of the PD cycler 102 includes the control unit 1090 that receives input signals from various PD cycler systems and devices including the touch screen 118, control buttons 120, the stepper motors 1094A, 1094B, the cassette chamber pressure sensors 149A, 149B, position sensors 1092A, 1092B (i.e., encoders) used to detect the position of the pistons 132A, 132B, vacuum tank pressure sensors 1081, and positive pressure tank pressure sensors 1082. Based on these and other inputs (i.e., previously stored instructions, etc.), the controller 1090 outputs control signals to various PD cycler systems and devices including the vacuum tanks 1016, 1017, the positive pressure tank 1082, the vent 1014, the air pump 1004, the manifolds 1012, 1080, the safety clamp 150, and the inflatable pad 132. Signals to and from the control unit 1090 may be sent via wired connection or wirelessly.

In addition to those features described above, the PD cycler 102 includes various other features not described in detail herein. Further details regarding the PD cycler 102 and its various components can be found in U.S. Patent Application Publication No. 2007/0112297, which is incorporated by reference herein.

Figure 8:
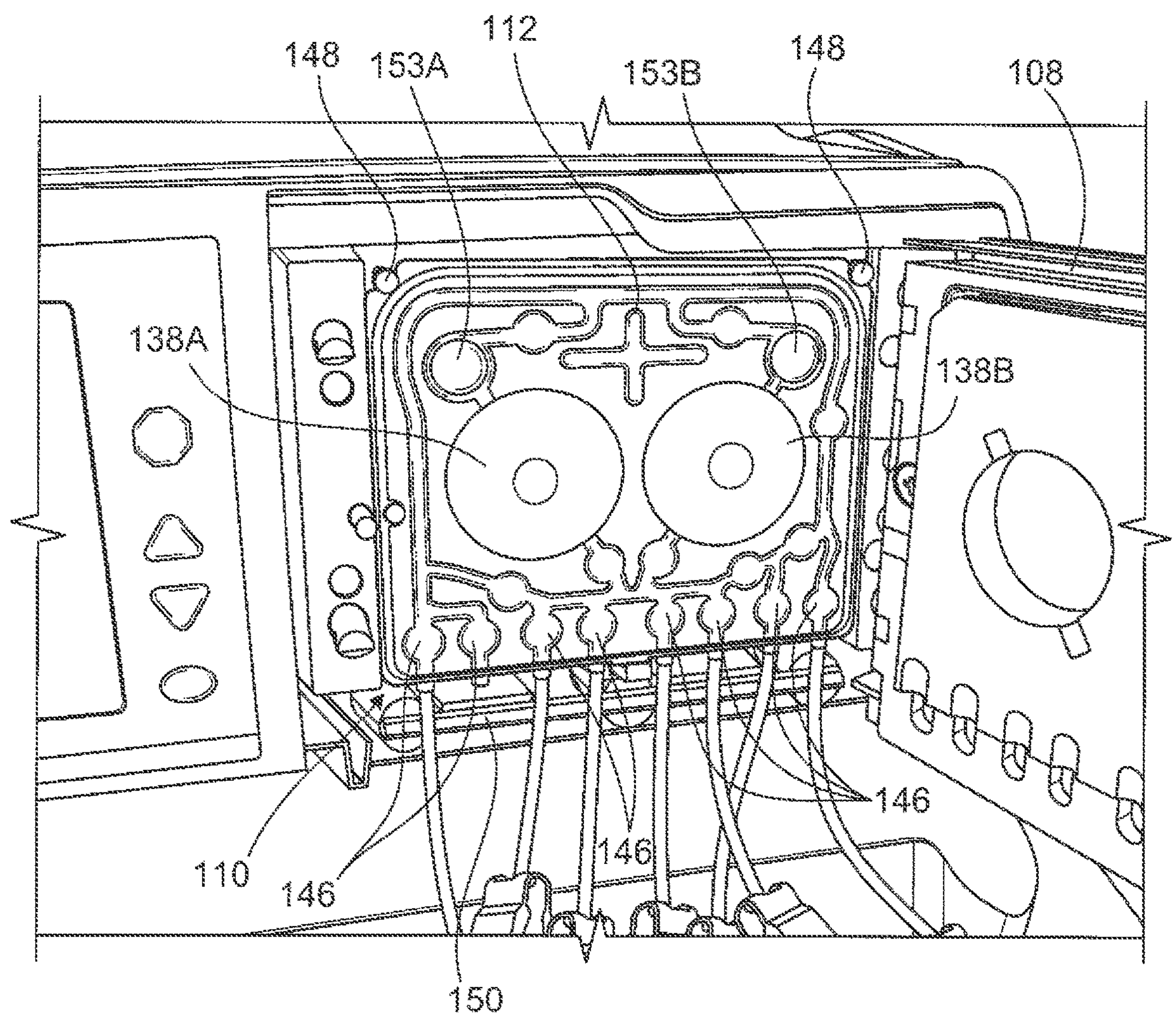
FIG. 8 is a partial perspective view of the PD cassette in the cassette compartment of the PD cycler of the PD system of FIG. 1.

A method of operating the PD cycler 102 will now be described. As shown in FIG. 8, before treatment, the door 108 of the PD cycler 102 is opened to expose the cassette interface 110, and the cassette 112 is positioned with its membrane 140 adjacent to the cassette interface 110. The cassette 112 is positioned such that the pump chambers 138A, 138B of the cassette 112 are aligned with the piston heads 134A, 134B, the depressible dome regions 146 of the cassette 112 are aligned with the inflatable members 142, and the pressure sensing cavities 153A, 153B of the cassette 112 are aligned with the pressure sensors 149A, 149B.

Referring also to FIG. 6, which schematically illustrates the air distribution system 1000 of the PD cycler 102, after loading the cassette 112 into the cassette compartment 114 of the PD cycler 102, positive pressure is supplied via the air line 1072 to the inflatable pad 135 in the door 108 of the PD cycler 102. In particular, positive pressure is supplied from the air pump 1004 and/or the positive pressure tank 1082 via the air line 1072 to the inflatable pad 135. The positive pressure inflates the inflatable pad 135 to secure the cassette 112 within the cassette compartment 114 in a manner such that the membrane 140 of the cassette 112 is pressed firmly against the cassette interface 110 of the PD cycler 102.

In addition, vacuum pressure is supplied to the vacuum ports 151 to form a seal between the membrane 140 and the cassette interface 110. Vacuum pressure is also supplied to the annular passages 147A, 147B formed around the pressure sensors 149A, 149B to draw the membrane 140 against those pressure sensors 149A, 149B. The vacuum pressure is supplied from the air pump 1004 and/or the vacuum tank 1017 to the vacuum ports 151 and the annular passages 147A, 147B. The vacuum pressure is directed through the air lines 1042, 1054, 1058, 1060, and 1062 to the vacuum ports 151. Similarly, the vacuum pressure is directed through the air lines 1042, 1066, and, 1068 to the annular passages 147A, 147B surrounding the pressure sensors 149A, 149B.

Vacuum pressure is also applied to the annular passages 137A, 137B surrounding the piston heads 134A, 134B. The vacuum pressure is supplied from the air pump 1004 and/or the vacuum tank 1016 to the annular passages 137A, 137B via the air lines 1046, 1047, 1048. With the cassette 112 loaded into the cassette compartment 114, the membrane 140 of the cassette 112 covers the annular passages 137A, 137B. As a result, when the piston heads 134A, 134B are retracted away from the cassette 112 during use, the vacuum pressure applied to the membrane 140 via the annular passages 137A, 137B causes the portions of the membrane 140 overlying the piston heads 134A, 134B to be drawn toward the cassette interface 110 in unison with the retracting piston heads 134A, 134B. As a result, the volume defined by the pump chambers 138A, 138B increases, and, depending on the state of the inflatable members 142, dialysate can be drawn into the pump chambers 138A, 138B as the piston heads 134A, 134B retract together with respective portions of the membrane 140. Similarly, depending on the state of the various inflatable members 142, as the piston heads 134A, 134B are advanced, the volume of the pump chambers 138A, 138B decreases, forcing dialysate from the pump chambers 138A, 138B.

As the pistons 132A, 132B of the PD cycler 102 reciprocate, each of the inflatable members 142 is either inflated or deflated to control the flow of dialysate through the cassette 112. To inflate the inflatable members 142, positive pressure is applied from the air pump 1004 and/or the positive pressure tank 1082 to the inflatable member valve manifold 1080 via the air line 1074. The valves of the inflatable member valve manifold 1080 are operated in a manner to deliver the positive pressure only to those inflatable members 142 that are to be or remain inflated. To deflate the inflatable members 142, vacuum pressure is supplied from the air pump 1004 and/or the vacuum tank 1017 to the inflatable member valve manifold 1080 via the air line 1048. The valves of the inflatable member valve manifold 1080 are operated in a manner to deliver the vacuum pressure only to those inflatable members 142 that are to be or remain deflated. Signals related to the pressure within the air line 1046 are transmitted from the vacuum sensor 1081 to the control unit 1090 of the PD cycler 102 throughout treatment.

In rare instances, the flexible membrane 140 of the PD fluid cassette 112 may have leaks due to small pin-holes or tears caused, for example, by damage during handling. Such pin-holes or tears can allow dialysate to leak through the flexible membrane 140 and enter the mechanical and pneumatic systems of the PD cycler 102. Dialysate leaks can render the PD cycler inoperable. In order to avoid using a leaky PD fluid cassette 112, the PD cycler 102 performs a cassette leak detection test on the PD fluid cassette 112 prior to use (e.g., prior to peritoneal dialysis treatment). In some cases, methods used by the PD cycler 102 to detect leaks in the cassette 112 include using air as the test fluid so that if a leak is detected, liquid is prevented from entering the mechanical and pneumatic systems of the PD cycler 102.

Figure 9:
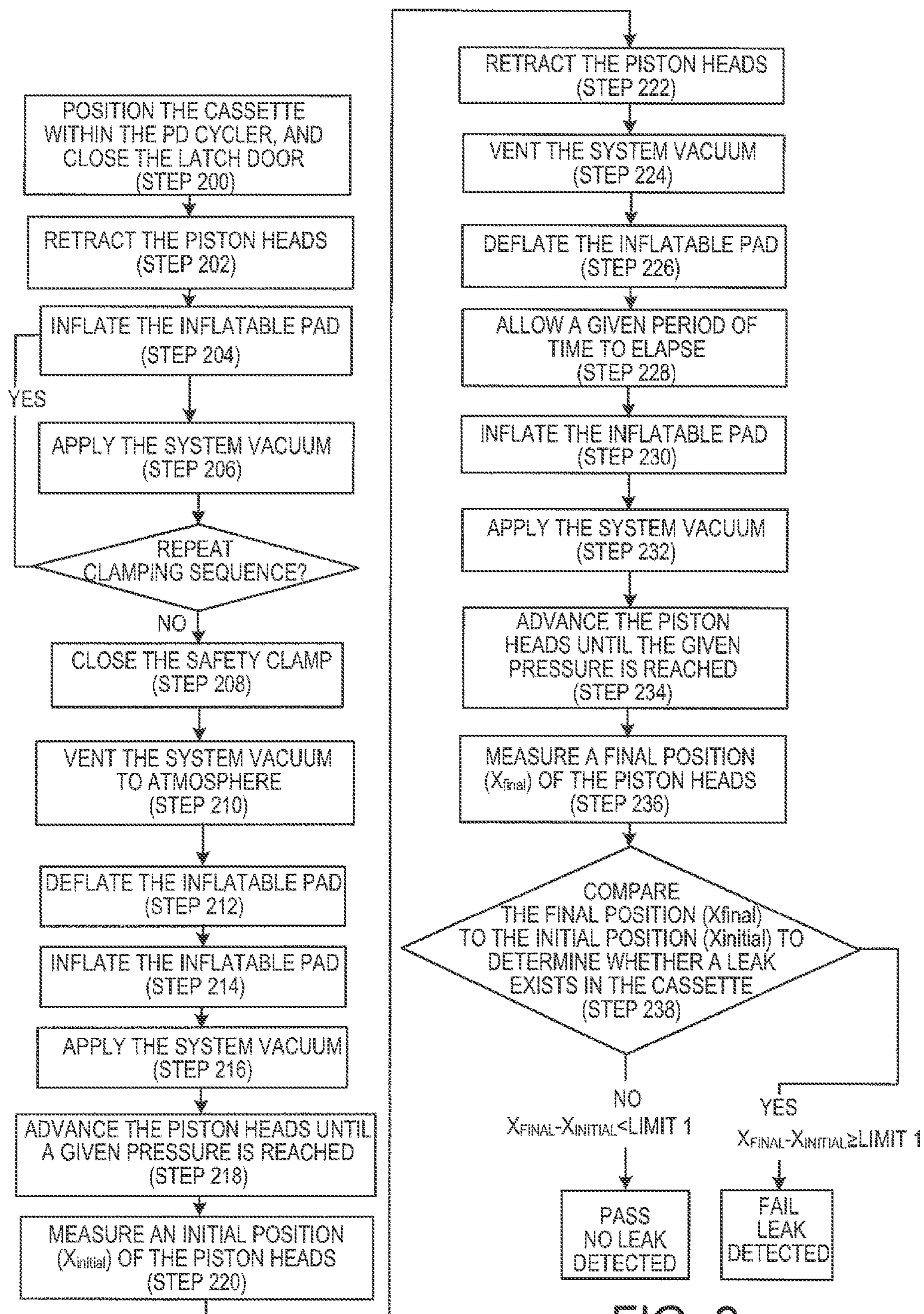
FIG. 9 is a flow chart that illustrates a position-based method of detecting leaks in a medical fluid cassette.

Referring to FIG. 9, a position-based method of detecting leaks in the PD fluid cassette 112 will now be described.

The PD fluid cassette 112 is positioned within the PD cycler 102 in the manner described above, e.g., in a manner consistent with normal use. The door 108 is then closed and latched (Step 200).

With the safety clamp 150 open, the piston heads 134A, 134B are fully retracted within the piston access ports 136A, 136B, e.g., away from the flexible membrane 140 of the PD fluid cassette 112 (Step 202). In some embodiments, this step is performed prior to positioning of the cassette 112 within the PD cycler 102 to reduce the risk of damage to the cassette flexible membrane 140 during positioning.

At this time, a procedure is performed that is intended to generate leaks in a flawed cassette 112, including those having sharp edges formed in the rigid base 156 or weaknesses in the flexible membrane 140. In particular, with the safety clamp open, the inflatable pad 135 within the door 108 is inflated (Step 204), and a "system vacuum" is applied to the cassette flexible membrane 140 (Step 206). Here, the term "system vacuum" refers to application of a vacuum using each of the vacuum ports 151, the annular passages 137A, 137B surrounding the piston access ports 136A, 136B, and the annular passages 147A, 147B surrounding the pressure sensors 149A, 149B. Since the system vacuum is applied to the membrane with the piston heads 134A, 134B in a retracted position, this procedure (Steps 204-206) permits maximization of a volume of atmospheric pressure air within the cassette 112. In some embodiments, to maximize the likelihood that any flaws in the cassette 112 are exposed, this procedure (Steps 204-206) may be repeated one or more times after deflating the inflatable pad 135 and venting the system vacuum.

Next, the safety clamp 150 is actuated, closing all inlets to and outlets from the cassette 112 (Step 208). By doing so, an initial volume of atmospheric pressure air is trapped within the cassette 112. The safety clamp 150 remains closed throughout the remainder of the position-based method.

Following closure of the safety clamp, a procedure is followed to ensure that a known initial volume of air is present within the cassette 112. In particular, the system vacuum is vented to the atmosphere (Step 210) via the vent 1014, the inflatable pad 135 is deflated (Step 212), the inflatable pad is re-inflated (Step 214), and the system vacuum is re-applied (Step 216). This procedure (Steps 210-216) releases air captured in any dead spaces within the cassette 112 between the flexible membrane 140 and the rigid base 156 (e.g., outside the fluid pathways 158, pump chambers 138A, 138B, etc.) that are not used for the function of the cassette and that initially hold air. As a result, this procedure (Steps 210-216) ensures that all air is within the cassette 112 is included in the measurement of initial air volume.

As a next step, the piston heads 134A, 134B are advanced into the flexible membrane 140 until a predetermined pressure is reached, as measured by the pressure sensors 149A, 149B (Step 218). In the illustrated embodiment, the predetermined pressure is 400 mbar.

When the pressure within the cassette 112 is at the predetermined pressure (e.g., 400 mbar), an initial position ($X_{initial}$) of the piston heads 134A, 134B relative to the PD cycler 102 is measured (Step 220), using the position sensors 1092A, 1092B connected to the stepper motors 1094A, 1094B. For example, the measured position may be provided in units of steps corresponding to detection by position sensors (e.g., encoders) 1092A, 1092B.

Following measurement of the initial position ($X_{initial}$), the piston heads 134A, 134B are retracted from the cassette 112 until a space exists between the piston heads 134A, 134B and the membrane 140 (Step 222). In some embodiments, the piston heads 134A, 134B are fully retracted within the piston access ports 136A, 136B to ensure maximum spacing. In addition, the system vacuum is vented to the atmosphere (Step 224), and the inflatable pad 135 is deflated (Step 226). By retracting the piston heads 134A, 134B, venting the system vacuum and deflating the inflatable pad 135, contact between the cassette 112 and the PD cycler 102 is reduced, minimized or eliminated.

After contact between the cassette 112 and the PD cycler 102 is reduced or minimized, a given period of time ("waiting period") is allowed to elapse before any subsequent steps (Step 228). During the waiting period, the cassette is permitted to leak air in an unobstructed manner should any leaks exist. In some embodiments, the given period of time is in a range of 10 seconds to 60 seconds (e.g, 20 seconds to 40 seconds, 30 seconds). Any of various other periods of time could alternatively be used as long as sufficient time is provided to allow detectable amounts of air to leak.

After the given period of time has elapsed, the initial test conditions are reestablished. In particular, the inflatable pad 135 within the door 108 is inflated (Step 230), and the system vacuum is applied to the cassette flexible membrane 140 (Step 232).

After inflation of the inflatable pad 135 and application of the system vacuum, the piston heads 134A, 134B are advanced into the flexible membrane 140 until the given pressure (e.g., 400 mbar) is reached, as measured by the pressure sensors 149A, 149B (Step 234). When the pressure within the cassette 112 is at the given pressure, a final position ($X_{final}$) of the piston heads 134A, 134B relative to the PD cycler 102 is measured (Step 236).

The PD cycler control unit 1090 compares the final position ($X_{final}$) to the initial position ($X_{initial}$) to determine whether a leak exists in the cassette (Step 238). In particular, the initial position ($X_{initial}$) is subtracted from the final position ($X_{final}$), and if the difference is equal to or greater than a predetermined amount (LIMIT1), the control unit 1090 determines that a leak exists in the cassette 112. If the difference is less than the predetermined amount (LIMIT1), no leak is detected. For example, the predetermined amount may be in a range of 1000 steps to 3500 steps.

Figure 10:
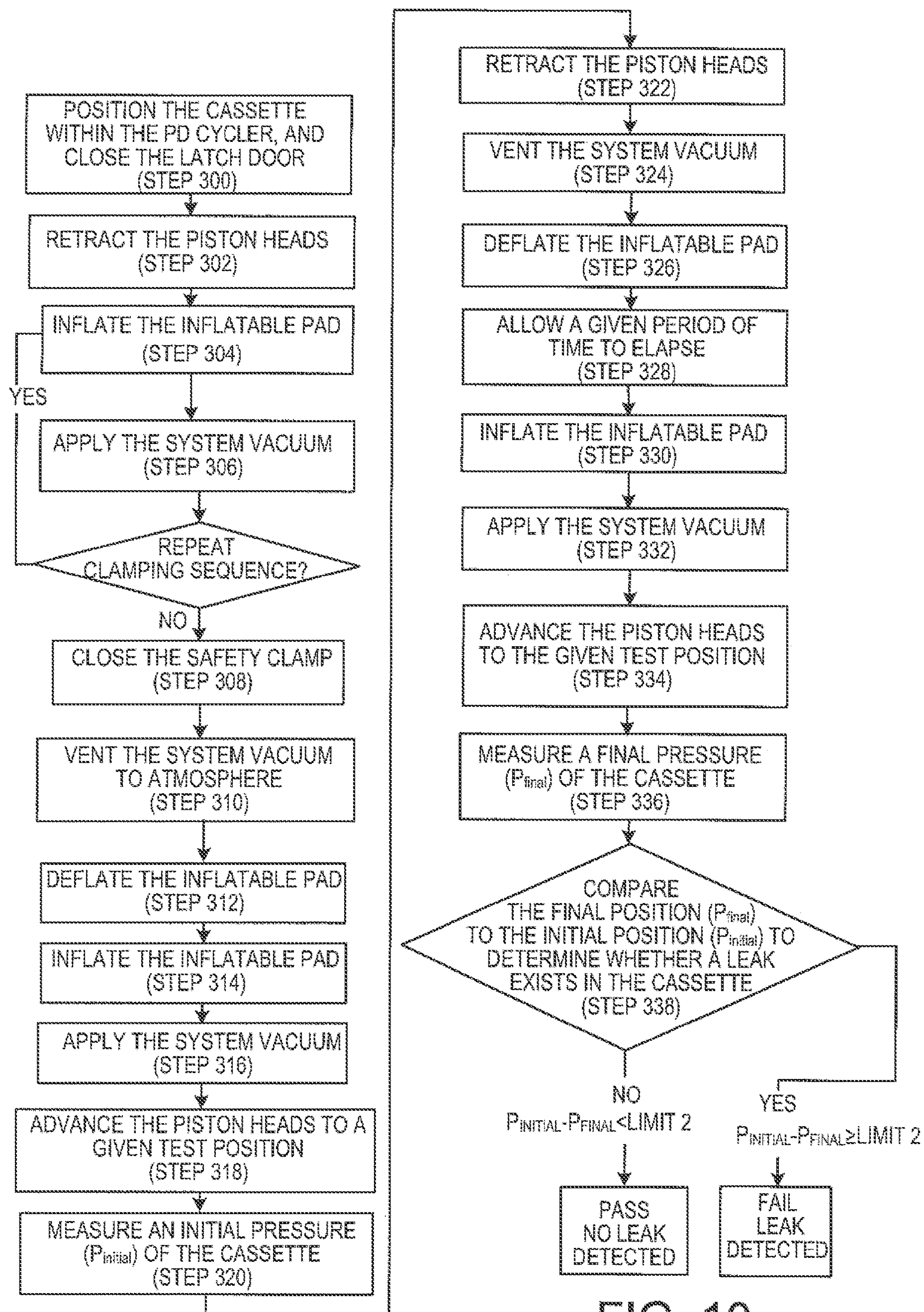
FIG. 10 is a flow chart that illustrates a volume-based method of detecting leaks in a medical fluid cassette.

While the above-described position-based leak detection method relies on the positions of the piston heads at a given pressure to determine whether a leak exists in the cassette 112, other methods can be used. For example, referring to FIG. 10, an alternative method (e.g., a pressure-based method) will now be described that relies on the pressure within the cassette for a given volume.

In the pressure-based method, the PD fluid cassette 112 is positioned within the PD cycler 102 in the manner described above, e.g., in a manner consistent with normal use. The door 108 is then closed and latched (Step 300).

With the safety clamp 150 open, the piston heads 134A, 134B are fully retracted within the piston access ports 136A, 136B, e.g., away from the flexible membrane 140 of the PD fluid cassette 112 (Step 302). In some embodiments, this step is performed prior to positioning of the cassette 112 within the PD cycler 102 to reduce the risk of damage to the cassette flexible membrane 140 during positioning.

At this time, a procedure is performed that is intended to generate leaks in a flawed cassette 112, including those having sharp edges formed in the rigid base 156 or weaknesses in the flexible membrane 140. In particular, with the safety clamp open, the inflatable pad 135 within the door 108 is inflated (Step 304), and the system vacuum is applied to the cassette flexible membrane 140 (Step 306). Since the system vacuum is applied to the membrane with the piston heads 134A, 134B in a retracted position, this procedure (Steps 304-306) permits maximization of a volume of atmospheric pressure air within the cassette 112. In some embodiments, to maximize the likelihood that any flaws in the cassette 112 are exposed, this procedure (Steps 304-306) may be repeated one or more times after deflating the inflatable pad 135 and venting the system vacuum.

Next, the safety clamp 150 is actuated, closing all inlets to and outlets from the cassette 112 (Step 308). By doing so, an initial volume of atmospheric pressure air is trapped within the cassette 112. The safety clamp 150 remains closed throughout the remainder of the pressure-based method.

Following closure of the safety clamp, a procedure is followed to ensure that a known initial volume of air is present within the cassette 112. In particular, the system vacuum is vented to the atmosphere (Step 310) via the vent 1014, the inflatable pad 135 is deflated (Step 312), the inflatable pad is re-inflated (Step 314), and the system vacuum is re-applied (Step 316). As discussed above, this procedure (Steps 310-316) releases air captured in any dead spaces within the cassette 112 between the flexible membrane 140 and the rigid base 156 (e.g., outside the fluid pathways 158, pump chambers 138A, 138B, etc.) that are not used for the function of the cassette and that initially hold air. As a result, this procedure (Steps 310-316) ensures that all air within the cassette 112 is included in the measurement of the initial air volume.

As a next step, the piston heads 134A, 134B are advanced into the flexible membrane 140 to a given test position relative to the PD cycler 102 (Step 318), defining a test volume of air within the cassette 112. In the illustrated embodiment, a given position of the piston heads is obtained by tracking steps of stepper motors 1094A, 1094B used to position the pistons 132A, 132B within the piston access ports 136A, 136B. For example, the given test position may be 34,000 steps as detected by corresponding sensors 1092A, 1092B. In other examples, a different number of steps can be used as the test position as long as the number of steps results in a sufficient test volume of air within the cassette 112.

While the piston heads 134A, 134B are in the given test position, an initial pressure ($P_{initial}$) is measured within the cassette 112 using the pressure sensors 149A, 149B (Step 320).

Following measurement of the initial pressure ($P_{initial}$), the piston heads 134A, 134B are retracted from the cassette 112 until a space exists between the piston heads 134A, 134B and the membrane 140 (Step 322). In some embodiments, the piston heads 134A, 134B are fully retracted within the piston access ports 136A, 136B to ensure maximum spacing. In addition, the system vacuum is vented to the atmosphere (Step 324), and the inflatable pad 135 is deflated (Step 326). By retracting the piston heads 134A, 134B, venting the system vacuum and deflating the inflatable pad 135, contact between the cassette 112 and the PD cycler 102 is reduced, minimized or eliminated.

After contact between the cassette 112 and the PD cycler 102 is reduced or minimized, a given period of time ("waiting period") is allowed to elapse before any subsequent steps (Step 328). During the waiting period, the cassette is permitted to leak air in an unobstructed manner should any leaks exist. In some embodiments, the given period of time is in a range of 10 seconds to 60 seconds (e.g, 20 seconds to 40 seconds, 30 seconds). Any of various other periods of time could alternatively be used as long as sufficient time is provided to allow detectable amounts of air to leak.

After the given period of time has elapsed, the initial test conditions are reestablished. In particular, the inflatable pad 135 within the door 108 is inflated (Step 330), and the system vacuum is applied to the cassette flexible membrane 140 (Step 332).

After inflation of the inflatable pad 135 and application of the system vacuum, the piston heads 134A, 134B are advanced into the flexible membrane 140 to the given test position relative to the PD cycler 102 (Step 334), to re-establish the original test volume of air within the cassette 112. When the piston heads 134A, 134B are in the given test position (e.g., 34,500 steps), a final pressure ($P_{final}$) is measured within the cassette 112 using the pressure sensors 149A, 149B (Step 336).

The PD cycler control unit 1090 compares the final pressure ($P_{final}$) to the initial pressure ($P_{initial}$) to determine whether a leak exists in the cassette (Step 338). In particular, the final pressure ($P_{final}$) is subtracted from the initial pressure ($P_{initial}$), and if the difference is equal to or greater than a predetermined amount (LIMIT2), the control unit 1090 determines that a leak exists in the cassette 112. If the difference is less than the predetermined amount (LIMIT2), no leak is detected. For example, for the given test position (e.g., 34,500 steps) of the piston heads 134A, 134B, the predetermined amount (LIMIT2) may be in a range of 6-10 mbar. However, it is understood that differences would be amplified if the piston heads 134A, 134B were driven further out. Although this would likely increase the value of LIMIT2, it would also increase the difference in mbar between difference readings in the no-leak and leak cases, respectively.

Figure 11:
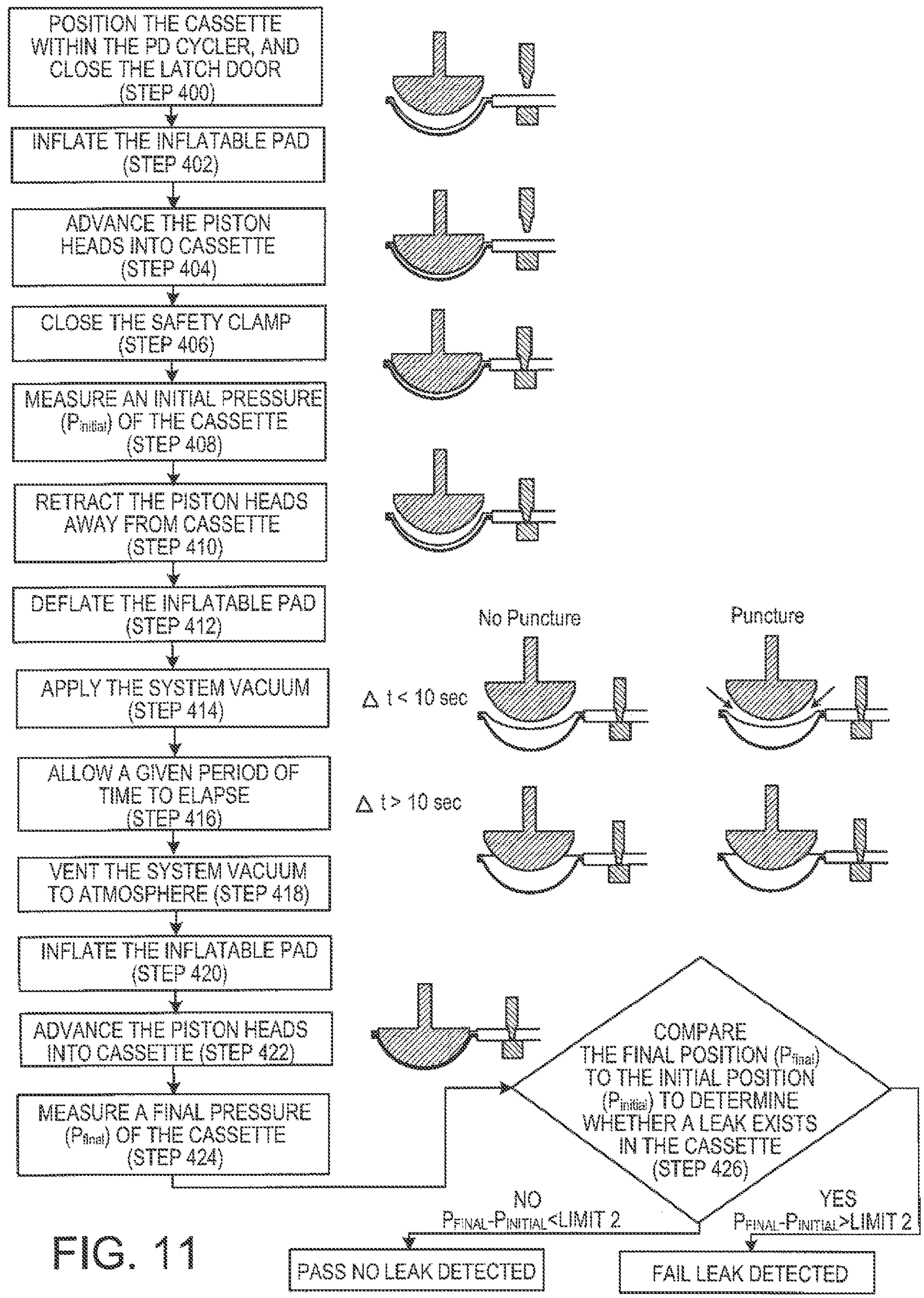
FIG. 11 is a flow chart that illustrates a minimum-volume method of detecting leaks in a medical fluid cassette.

While the above-described leak detection method is a pressure-based method that relies on the pressure within the cassette for a given volume to determine whether a leak exists in the cassette 112, other pressure-based methods can be used. For example, referring to FIG. 11, an alternative pressure-based method (e.g., a minimum-volume method) will now be described that relies on the pressure within the cassette for a given volume to determine whether a leak exists in the cassette 112, where the given volume is a minimized volume.

In the minimum-volume method, the PD fluid cassette 112 is positioned within the PD cycler 102 in the manner described above, e.g., in a manner consistent with normal use. The door 108 is then closed and latched (Step 400).

With the safety clamp 150 open, the inflatable pad 135 within the door 108 is inflated, deflated, and re-inflated (Step 402). This step (Step 402) distributes atmospheric air within the cassette 112, expels atmospheric air from the cassette 112, and may also generate leaks in a flawed cassette 112, including those having sharp edges formed in the rigid base 156 or weaknesses in the flexible membrane 140.

As a next step, the piston heads 134A, 134B are advanced toward the flexible membrane 140 until the pistons 132A, 132B are fully outward (Step 404). In this position, the piston heads 134A, 134B have driven the flexible membrane 140 toward the rigid base 156 until the flexible membrane 140 is in contact with a surface of each of the pump chambers 138A, 138B. As a result, the air volume within the cassette 112 is minimized.

While the piston heads 134A, 134B are in the fully-outward position, the safety clamp 150 is actuated, closing all inlets to and outlets from the cassette 112 (Step 406). By doing so, a minimum initial volume of atmospheric pressure air is trapped within the cassette 112. The safety clamp 150 remains closed throughout the remainder of the minimum-volume method.

While the piston heads 134A, 134B are in the fully-outward position resulting in a minimum volume of air within the cassette 112, an initial pressure ($P_{initial}$) is measured within the cassette 112 using the pressure sensors 149A, 149B (Step 408). $P_{initial}$ should be approximately equal to atmospheric pressure. For example, $P_{initial}$ is typically within 10 mbar of atmospheric pressure.

Following measurement of the initial pressure ($P_{initial}$), the piston heads 134A, 134B are retracted from the cassette 112 until a space exists between the piston heads 134A, 134B and the membrane 140 (Step 410). In some embodiments, the piston heads 134A, 134B are fully retracted within the piston access ports 136A, 136B to ensure maximum spacing. By retracting the piston heads 134A, 134B, and deflating the inflatable pad 135, contact between the cassette 112 and the PD cycler 102 is reduced, minimized, or eliminated. For example, retraction of the piston heads 134A, 134B separates the piston heads 134A, 134B from the flexible membrane 140 whereby any leaks in the vicinity of the pump chambers 138A, 138B are exposed, and deflation of the inflatable pad 135 allows leakage from leaks that may exist in regions outside the normal flowpaths of the cassette 112.

Following or concurrent with retraction of the piston heads 134A, 134B, the inflatable pad 135 is deflated (Step 412). Deflation of the inflatable pad 135 redistributes air throughout the cassette 112, and allows leaks outside the normal flow path to exchange air with the pump chamber.

When the piston heads 134A, 134B have been retracted and the inflatable pad 135 deflated, the system vacuum is applied to the cassette 112 (Step 414). The system vacuum serves to separate the flexible membrane 140 from the rigid base 156. In addition, due to the elasticity of the flexible membrane 140 and removal of the piston heads 134A, 134B, the flexible membrane 140 will tend to return to its original flat configuration, and retract away from the surface of the pump chambers 134A, 134B. Because the safety clamp 150 is closed, separation of the flexible membrane 140 from the rigid base 156 results in generation of a negative pressure within the cassette 112. At this time, if leaks are present within the cassette 112, air is drawn into the space between the flexible membrane 140 and the rigid base 156 due to the negative pressure within the cassette 112.

After application of the system vacuum, a predetermined period of time ("retraction period") is allowed to elapse before any subsequent steps (Step 416). During the retraction period, the cassette is permitted to leak air in an unobstructed manner should any leaks exist. In some embodiments, the predetermined period of time is in a range of 2 seconds to 20 seconds. In other embodiments, the predetermined period of time is in a range of 5 seconds to 15 seconds. In still other embodiments the predetermined period of time is 10 seconds.

Once the predetermined period of time has elapsed, the system vacuum is vented to the atmosphere (Step 418) and the inflatable pad 135 is inflated (Step 420). This procedure (Steps 418-420) prepares the cassette for the following steps.

Next, the piston heads 134A, 134B are advanced toward the flexible membrane 140 until the pistons 132A, 132B are fully outward (Step 422). As previously discussed, in this position, the piston heads 134A, 134B have driven the flexible membrane 140 toward the rigid base 156 until the flexible membrane 140 is in contact with a surface of each of the pump chambers 138A, 138B.

While the piston heads 134A, 134B are in the fully-outward position resulting in a minimum volume of air within the cassette 112, a final pressure ($P_{final}$) is measured within the cassette 112 using the pressure sensors 149A, 149B (Step 424).

The PD cycler control unit 1090 compares the final pressure ($P_{final}$) to the initial pressure ($P_{initial}$) to determine whether a leak exists in the cassette (Step 426). In particular, the initial pressure ($P_{initial}$) is subtracted from the final pressure ($P_{final}$), and if the difference is equal to or greater than a predetermined amount (LIMIT3), the control unit 1090 determines that a leak exists in the cassette 112. If the difference is less than the predetermined amount (LIMIT3, no leak is detected. For example, the predetermined amount (LIMIT3) may be in a range of 126 to 150 mbar. Table 1 shows test data obtained using the minimum volume method. Test data are provided for the following cassette flexible membrane conditions: an intact flexible membrane (e.g., leak free) as seen in the first row of Table 1, a cassette flexible membrane having a small puncture/stretch (e.g. a 0.4 mm leak) as seen in the second row of Table 1, and a cassette flexible membrane having a large clean hole (e.g. a 0.7 mm hole) as seen in the third row of Table 1. The results show that small, non-zero pressure differences are obtained for cassettes having no leak. The non-zero differences may be related to inefficiencies in pressure redistribution within the cassette during step 412. In addition, although small differences between the initial pressure ($P_{initial}$) and the final pressure ($P_{final}$) are normal, excessive differences between the initial pressure ($P_{initial}$) and the final pressure ($P_{final}$) indicate a leak exists in the cassette 112, with larger leaks resulting in greater pressure differences. Although the test was performed to verify that the minimum-volume method is effective for identifying leaks in the cassette 112, it was not optimized to identify a minimum LIMIT3 required to avoid a false positive result. That is, while the test was sufficient to establish sensitivity and specificity for a rather small hole in the membrane (400 micron puncture/stretch), it was not necessarily an optimized procedure, especially for specificity. The 126 mbar value for LIMIT3 can be reduced, for example by repeating the test several times, thus expelling some of the air originally trapped in the non-flow-path regions. This will have the effect of reducing the value of the non-leak pressure difference from 126 mbar.

TABLE 1

| Cassette Condition | Pressure Difference Sensor 1 (149A) (mbar) | Pressure Difference Sensor 2 (149B) (mbar) |
|---|---|---|
| No leak | 116 ± 10 | 106 ± 10 |
| 0.4 mm puncture/stretch | 251 ± 30 | 243 ± 30 |
| 0.7 mm clean hole | 860 ± 50 | 851 ± 50 |

In some implementations, the minimum volume method of detecting leaks in the PD fluid cassette 112 can be simplified while still providing accurate and reliable leak detection. For example, step 412 (deflating the inflatable pad 135 in order to redistribute air throughout the cassette) performed before system vacuum activation, and steps 418-420 (venting the system vacuum and inflating the inflatable pad 135 in order to prepare for re-application of the force and second pressure measurement) performed after system vacuum activation, can be omitted. By doing so, the overall time required to perform the method can be reduced. In addition, the 126 mbar value for LIMIT3 can be reduced significantly, by first performing this "simplified minimum-volume test", in which the non-flow-path regions are not accessed, specifically in order to detect leaks in the piston head region, and then performing another test such as the minimum-volume test, specifically in order to detect leaks in the non-flow-path regions. In some implementations, by performing more than one type of test, it may be possible to identify the general location (e.g., within a flow-path region or within a non-flow path region) of a leak based on which test results in detection of the leak.

In each of the above-described methods of detecting leaks in a disposable medical fluid cassette, a first force is applied to the flexible membrane 140, a first physical property of a system that includes the medical fluid cassette 112 and the PD cycler 102 is measured, and then the first force is removed from the flexible membrane 140. Following a brief waiting period, a second force is applied to the flexible membrane 140, a second physical property of the system is measured, and then it is determined whether the medical fluid cassette leaks based on a comparison of the first physical property and the second physical property. In the position-based method, the first physical property measured is the initial position ($X_{initial}$) of the piston heads 134A, 134B relative to the PD cycler 102 and the second physical property is the final position ($X_{final}$) of the piston heads 134A, 134B relative to the PD cycler 102. In the pressure-based method and minimum-volume method, the first physical property measured is the initial pressure ($P_{initial}$) within the cassette 112, and the second physical property is the final pressure ($P_{final}$) within the cassette 112.

In each of the illustrated embodiments discussed above, the first force is the same as the second force, but the method is not limited to doing so. For example, in the minimum-volume method, the forces applied by the piston can be different as long as the air volume in the cassette is minimized.

In each method described above, the forces applied to the cassette 112 (e.g., via the piston, inflatable door pad 135 and system vacuum) are removed between the initial and final measurements to ensure that a space exists between the flexible membrane 140 and the PD cycler, avoiding obstruction of any leaks in the flexible membrane 140 between measurements of the physical properties of the system. This method is advantageous over some conventional leak detection methods where the force is continuously applied to a medical fluid cassette using pistons of a medical fluid pumping machine (e.g. a PD cycler) and a leak is located in the medical fluid cassette membrane in the vicinity of the pump chambers. In such conventional approaches, the piston itself may obstruct the leak and provide a false confidence in membrane integrity. By removing the applied force (for example, by retracting the pistons) between the initial and final measurements, the accuracy of leak detection measurements is improved since membrane leaks in the vicinity of the applied force not obstructed, permitting detection of leaks in the vicinity of the applied force.

While in each of the methods of detecting leaks in a disposable medical fluid cassette described herein, the first force and second force are applied to the flexible membrane 140 using the pistons 132A, 132B of the PD cycler 102, the method is not limited to using pistons to apply the first force and second force. For example, in some embodiments, the first force and second force are applied to the flexible membrane 140 pneumatically or using other mechanisms.

While the position-based method recites one repetition of steps 222-234 (e.g, the steps between the measurement of the initial position ($X_{initial}$) and the measurement of the final position ($X_{final}$)), the method is not limited to one repetition. For example, steps 222-234 may be repeated more than once, resulting in greater sensitivity and certainty. Similarly, while the volume-based method recites one repetition of steps 322-334 (e.g, the steps between the measurement of the initial pressure ($P_{initial}$) and the measurement of the final pressure ($P_{final}$)), the method is not limited to one repetition. For example, steps 322-334 may be repeated more than once, resulting in greater sensitivity and certainty.

While the position-based method recites performing steps 222-234 (e.g, the steps between the measurement of the initial position ($X_{initial}$) and the measurement of the final position ($X_{final}$)) once including waiting a single, predetermined period of time, it may be possible to minimize overall leak-detection test time by repeating steps 222-234 multiple times using a shorter (e.g. minimized) waiting period. Similarly, while the volume-based method recites performing steps 322-334 (e.g, the steps between the measurement of the initial pressure ($P_{initial}$) and the measurement of the final pressure ($P_{final}$)) once including waiting a single, predetermined period of time, it may be possible to minimize overall leak-detection test time by repeating steps 322-334 multiple times using a shorter (e.g. minimized) waiting period.

While the minimum-volume method includes applying a system vacuum when the piston heads 134A, 134B have been retracted and the inflatable pad 135 deflated (Step 414), the minimum-volume method is not limited to this. For example, in some implementations, the step of applying a system vacuum may be omitted, whereby the flexible membrane 140 separates from the rigid base 156 due to the elasticity of the flexible membrane 140, resulting in generation of a negative pressure within the cassette 112. If leaks are present within the cassette 112, air is drawn into the space between the flexible membrane 140 and the rigid base 156 due to the negative pressure within the cassette 112.

While the air distribution system 1000 has been described as including the pump 1004 for generating and supplying positive and negative pressure, other types of pressure generating devices can alternatively or additionally be used. One example of another suitable device is the Hargraves BTC-IIS, single body, dual head Miniature Diaphragm Pump and Compressor.

While a system vacuum is described as application of a vacuum using each of the vacuum ports 151, the annular passages 137A, 137B, and the annular passages 147A, 147B, in some embodiments, the system vacuum may be applied through only a subset of these ports.

While the air distribution system 1000 uses pressurized air and vacuum to actuate the inflatable members 142 and the inflatable pad 135 and to draw the membrane 140 against the piston heads 134A, 134B and other surfaces of the cassette interface 110, gases other than air can alternatively or additionally be supplied throughout the air distribution system. Also, the inflatable members 142 and inflatable pad 135 can be replaced with mechanically actuated devices. Similarly, the pistons can be replaced with hydraulic or pneumatic devices such as diaphragm pumps.

While in each of the illustrated embodiments described above the first force and the second force are applied to an external surface of the cartridge 112, and particularly to the external surface of the flexible membrane 140, the method is not limited to external force application. In certain implementations, for example those in which the force is applied hydraulically or pneumatically, forces may be applied to internal surfaces of the cassette 112.

In certain implementations, vacuum pressure is not used to draw the cassette membrane 140 toward the piston heads 134A, 134B. Instead, other types of non-vacuum mechanisms, such as adhesive, magnetic or mechanical coupling, can be used to ensure that the cassette membrane 140 retracts along with the piston heads 134A, 134B.

In certain implementations, the characteristics of the cassette components are relied upon to drive fluid flow through a leak. For example, in the minimum-volume test, the elasticity of the flexible membrane 40 is used to provide a positive or negative pressure in the working fluid that may drive fluid flow through a leak at a detectable level.

While the vacuum and pressure sensors of the air distribution system 1000 have been described as being connected to air lines leading to vacuum and positive pressure tanks, other arrangements are possible. In certain implementations, for example, the vacuum and pressure sensors are all part of an input/output board of the PD cycler 102.

While the piston heads 134A, 134B of the PD cyclers above have been described as being hemispherical, the piston heads could be any of various other shapes. In some implementations, for example, the piston heads can have flat end surfaces. In such implementations, the cup-shaped members disposed in the pump chambers of the cassette can have flat surfaces that abut the flat end surfaces of the piston heads during use. Similarly, while the piston heads 134A, 134B have been described as being formed using certain materials and manufacturing techniques, any of various other suitable materials and manufacturing techniques could alternatively be used.

While the methods for detecting leaks described herein employ both pistons 132A, 132B of the PD cycler 102 used at the same time and in the same way, the methods can be performed using both pistons 132A, 132B used at different times and/or in different ways, or using only a single piston (i.e., piston 132A).

While the cassettes discussed above have been described as having two pump chambers, the cassettes can alternatively have more or fewer than two pump chambers.

While certain PD cyclers above have been described as including a touch screen and associated buttons, the PD cycler can include other types of screens and user data entry systems. In certain implementations, for example, the cycler includes a display screen with buttons (e.g., feathertouch buttons) arranged on the console adjacent the display screen. Certain buttons can be arranged to be aligned with operational options displayed on the screen during use such that the user can select a desired operational option by pressing the button aligned with that operational option. Additional buttons in the form of arrow buttons can also be provided to allow the user to navigate through the various display screens and/or the various items displayed on a particular screen. Other buttons can be in the form of a numerical keypad to allow the user to input numerical values in order, for example, to input operational parameters. A select or enter button can also be provided to allow the user to select an operational option to which the user navigated by using the arrow keys and/or to allow the user to enter values that the user inputted using the numerical keypad.

While the doors of the PD cyclers described above are shown as being positioned on a front face of the PD cyclers, the doors can alternatively be positioned at various other locations on the PD cyclers. For example, the doors could be positioned on a top face of the PD cycler such that the cassette is slid into the cassette compartment in a substantially horizontal orientation instead of a substantially vertical orientation.

While some of the PD cyclers discussed above have been described as including inflatable pads in their doors to compress the cassette between the door and the cassette interface, the PD cyclers can alternatively or additionally include inflatable pads positioned behind the cassette interface.

While the cassettes described above have been described as being part of a PD system, these types of cassettes can be used in any of various other types of cassette-based medical fluid pumping systems. Other examples of medical fluid pumping systems with which cassettes described herein can be used include hemodialysis systems, blood perfusion systems, and intravenous infusion systems.

While the cassettes have been described as being used to pump dialysate, other types of dialysis fluids can be pumped through the cassettes. As an example, in the case of cassettes used with hemodialysis machines, blood can be pumped through the cassettes. In addition, priming solutions, such as saline, can similarly be pumped through cassettes using the various different systems and techniques described above. Similarly, as an alternative to dialysis fluids, any of various other types of medical fluids can be pumped through the above-described cassettes depending on the type of medical fluid pumping machines with which the cassettes are used.

A selected illustrative embodiment of the invention is described above in some detail. It should be understood that only structures considered necessary for clarifying the present invention have been described herein. Other conventional structures, and those of ancillary and auxiliary components of the system, are assumed to be known and understood by those skilled in the art. Moreover, while a working example of the present invention has been described above, the present invention is not limited to the working example described above, but various design alterations may be carried out without departing from the present invention as set forth in the claims.

What is claimed is:

1. A medical fluid pumping machine configured to receive a disposable medical fluid cassette, the medical fluid cassette comprising a base and a flexible membrane attached to the base in such a way that the base and the flexible membrane cooperate to at least partially form a fluid passageway, the medical fluid pumping machine comprising:

- a compartment that receives the medical fluid cassette,
- a pressure applicator configured to apply a force to the medical fluid cassette when the medical fluid cassette is disposed within the compartment;
- a processer that is configured to
  - control the pressure applicator in such a way that a first force is applied to the flexible membrane when the medical fluid cassette is disposed within the compartment;
  - measure a first physical property of a system that includes the medical fluid pumping machine with the medical fluid cassette disposed within the compartment while the first force is applied to the flexible membrane;
  - control the pressure applicator in such a way that the first force is removed from the flexible membrane when the medical fluid cassette is disposed within the compartment;
  - control the pressure applicator in such a way that a second force is applied to the flexible membrane when the medical fluid cassette is disposed within the compartment;
  - measure a second physical property of the system that includes the medical fluid pumping machine with the medical fluid cassette disposed within the compartment while the second force is applied to the flexible membrane; and
  - determine whether the medical fluid cassette leaks based on a comparison of the first physical property and the second physical property.

2. The medical fluid pumping machine of claim 1, comprising

- a door that is configured to selectively close the compartment and retain the medical fluid cassette within the compartment, and
- an inflatable bladder disposed on an inside surface of the door and configured such that
  - when inflated while the medical fluid cassette is within the compartment, the inflatable bladder is configured to compress the medical fluid cassette, and
  - when deflated while the medical fluid cassette is within the compartment, the inflatable bladder is configured to contract against the inside surface of the door and generate a space between the inflatable bladder and the medical fluid cassette, wherein
- the processer is configured to deflate the door bladder between controlling the pressure applicator in such a way that the first force is removed from the flexible membrane and controlling the pressure applicator in such a way that the second force is applied to the flexible membrane.

3. The medical fluid pumping machine of claim 1 wherein the medical fluid cassette includes fluid inlet ports and fluid outlet ports that provide communication between the fluid passageway and an exterior of the medical fluid cassette, and

- the processer is configured to close the fluid inlet ports and fluid outlet ports after controlling the pressure applicator in such a way that the first force is applied to the flexible membrane and before measuring the first pressure within the medical fluid cassette.

4. The medical fluid pumping machine of claim 1 wherein the medical fluid cassette includes fluid inlet ports and fluid outlet ports that provide communication between the fluid passageway and an exterior of the medical fluid cassette, and controlling the pressure applicator in such a way that the first force is applied to the flexible membrane is performed with the fluid inlet ports and fluid outlet ports closed.

5. The medical fluid pumping machine of claim 1, comprising a vacuum source controllable by the processor and disposed within the compartment in a manner such that, when activated while the medical fluid cassette is within the compartment, the vacuum source is configured to apply a force to the flexible membrane, and the processor is configured to change a spacing between the flexible membrane and the base by activating the vacuum source.

6. The medical fluid pumping machine of claim 5, wherein the processor is configured to change the spacing after controlling the pressure applicator in such a way that the first force is removed from the flexible membrane and before controlling the pressure applicator in such a way that the second force is applied to the flexible membrane.

7. The medical fluid pumping machine of claim 5, wherein the vacuum source is configured to apply a force to an outer surface of the flexible membrane.

8. The medical fluid pumping machine of claim 1 wherein controlling the pressure applicator in such a way that the first force is applied to the flexible membrane comprises controlling the pressure applicator in such a way that the flexible membrane is compressed against the base.

9. The medical fluid pumping machine of claim 8 wherein the pressure applicator comprises a piston configured to be advanced into and retracted from the compartment.

10. The medical fluid pumping machine of claim 8 wherein the medical fluid cassette includes fluid inlet ports and fluid outlet ports that provide communication between the fluid passageway and an exterior of the medical fluid cassette, and controlling the pressure applicator in such a way that the first force is applied to the flexible membrane is performed with the fluid inlet ports and fluid outlet ports open.

* * * * *